(12) United States Patent
Iguchi et al.

(10) Patent No.: US 11,567,288 B2
(45) Date of Patent: Jan. 31, 2023

(54) ENDOSCOPE APPARATUS

(71) Applicant: OLYMPUS CORPORATION, Tokyo (JP)

(72) Inventors: Takehiko Iguchi, Hino (JP); Sho Nakamura, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 538 days.

(21) Appl. No.: 16/735,928

(22) Filed: Jan. 7, 2020

(65) Prior Publication Data
US 2020/0142152 A1 May 7, 2020

Related U.S. Application Data

(63) Continuation of application No. PCT/JP2017/025032, filed on Jul. 7, 2017.

(51) Int. Cl.
*H02K 11/215* (2016.01)
*G02B 7/04* (2021.01)
(Continued)

(52) U.S. Cl.
CPC ............ *G02B 7/04* (2013.01); *A61B 1/00188* (2013.01); *G02B 23/2438* (2013.01);
(Continued)

(58) Field of Classification Search
CPC .............. A61B 1/00188; A61B 1/0019; A61B 1/00006; H04N 5/2253; H04N 5/2254;
(Continued)

(56) References Cited

U.S. PATENT DOCUMENTS 9,887,612 B1 * 2/2018 Eghbal .............. H02K 41/0356
2015/0130388 A1  5/2015 Fukushima
(Continued)

FOREIGN PATENT DOCUMENTS

EP        2851725 A1    3/2015
JP     2010-107894 A    5/2010
(Continued)

OTHER PUBLICATIONS

Machine Translation of WO 2015178126 A1 (Year: 2015).*
International Search Report dated Sep. 19, 2017 issued in PCT/JP2017/025032.

*Primary Examiner* — Ahmed Elnakib
*Assistant Examiner* — Christopher S Leone
(74) *Attorney, Agent, or Firm* — Scully, Scott, Murphy & Presser, P.C.

(57) ABSTRACT

An endoscope apparatus has an endoscope and a video processor. The endoscope has a magnet and a coil, the magnet has a voice coil motor configured to be movable with respect to the coil and a Hall device disposed in the vicinity of the coil and configured to detect a magnetic field of the magnet in order to detect a position of the magnet. The video processor includes a position detection circuit configured to detect the position of the magnet from an outputted signal of (Continued)

the Hall device, an arithmetic operation section configured to correct a sensor output signal indicating the position of the magnet detected by the position detection circuit using correction information and output the sensor output signal, and a drive control circuit configured to control a current or a voltage to the coil based on an arithmetic operation result of the arithmetic operation section.

12 Claims, 14 Drawing Sheets

(51) Int. Cl.
- *H02K 11/27* (2016.01)
- *H02K 11/33* (2016.01)
- *A61B 1/00* (2006.01)
- *G02B 23/24* (2006.01)
- *H02K 41/035* (2006.01)

(52) U.S. Cl.
CPC ........... *H02K 11/215* (2016.01); *H02K 11/27* (2016.01); *H02K 11/33* (2016.01); *H02K 41/0354* (2013.01)

(58) Field of Classification Search
CPC ............. H02K 41/035; H02K 41/0352; H02K 41/0354; H02K 41/0356; H02K 11/225; H02K 11/215; H02K 11/22
See application file for complete search history.

(56) References Cited

U.S. PATENT DOCUMENTS

| | | | | |
|---|---|---|---|---|
| 2015/0198783 | A1* | 7/2015 | Shimotsu | G02B 7/023 359/814 |
| 2015/0351879 | A1* | 12/2015 | Boltanski | A61C 9/0053 433/29 |
| 2016/0041381 | A1* | 2/2016 | Makiyama | G02B 23/2438 359/824 |
| 2018/0270453 | A1* | 9/2018 | Kupferschmid | A61B 1/00193 |

FOREIGN PATENT DOCUMENTS

| | | | |
|---|---|---|---|
| JP | 2012-184983 A | 9/2012 | |
| WO | WO 2013/171998 A1 | 11/2013 | |
| WO | WO-2015178126 A1 * | 11/2015 | ............... A61B 1/00 |
| WO | WO 2016/098225 A1 | 6/2016 | |
| WO | 2017/104090 A1 | 6/2017 | |

\* cited by examiner

ENDOSCOPE APPARATUS

CROSS REFERENCE TO RELATED APPLICATION

This application is a continuation application of PCT/JP2017/025032 filed on Jul. 7, 2017, the entire contents of which are incorporated herein by this reference.

BACKGROUND OF INVENTION

1. Field of the Invention

The present invention relates to an endoscope apparatus and relates to an endoscope apparatus that has a drive mechanism using a voice coil motor.

2. Description of the Related Art

Endoscope apparatuses have been widely used in the medical field and the industrial field. In the medical field, for example, diseases are discovered and diagnosed by inserting elongated insertion sections into subjects and causing display devices to display endoscope images in the subjects.

There are endoscope apparatuses that have mechanisms configured to change image pickup magnification in order to observe subjects in an enlarged manner and perform focusing control.

For example, International Publication No. 2016/098225 proposes an endoscope that has an optical unit using a voice coil motor. The voice coil motor is used to drive a movable lens for focusing control, zooming control, and the like such that the movable lens moves forward and backward in an optical axis direction.

SUMMARY OF THE INVENTION

An endoscope apparatus according to an aspect of the invention includes: an endoscope; a voice coil motor provided in the endoscope and including a magnet and a coil such that the magnet is movable with respect to the coil; a magnetic sensor disposed in a vicinity of the coil and configured to detect a magnetic field of the magnet in order to detect a position of the magnet; a memory configured to store correction information; a position detection circuit configured to detect the position of the magnet from an outputted signal of the magnetic sensor; a processor configured to correct a position signal indicating the position of the magnet detected by the position detection circuit using the correction information stored in the memory and output the position signal; and a drive control circuit configured to control a current or a voltage to the coil based on an arithmetic operation result of the processor.

DETAILED DESCRIPTION OF THE PREFERRED EMBODIMENT

Hereinafter, an embodiment of the invention will be described with reference to the drawings.

(Overall Configuration)

Figure 1:
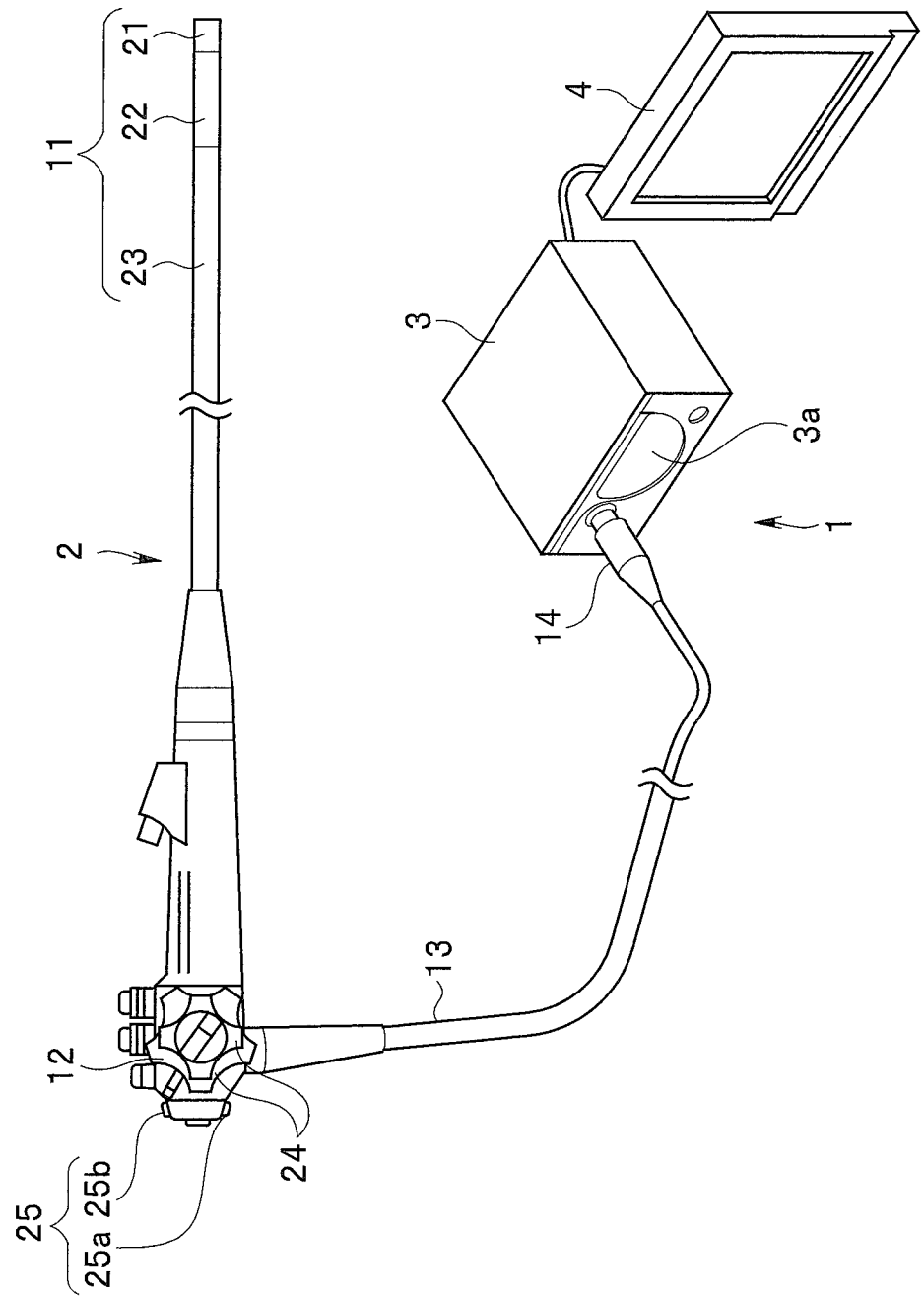
FIG. 1 is a configuration diagram illustrating a configuration of an endoscope apparatus 1 according to an embodiment of the invention.

FIG. 1 is a configuration diagram illustrating a configuration of an endoscope apparatus 1 according to the embodiment. As illustrated in FIG. 1, the endoscope apparatus 1 according to the embodiment is configured to have an endoscope 2 and a video processor 3 to which the endoscope 2 is connected. A monitor 4 is connected to the video processor 3.

The endoscope 2 is an electronic endoscope that has an elongated insertion section 11, an operation section 12 connected to a proximal end of the insertion section 11, and a universal cable 13 extending from the operation section 12.

The insertion section 11 of the endoscope 2 has a rigid distal end portion 21 at a distal end of the insertion section 11, a bending section 22 that is freely bent is provided so as to be adjacent to the distal end portion 21, and a long flexible pipe section 23 is further provided on a side of the proximal end of the bending section 22.

The distal end portion 21 incorporates an image pickup device 34 (FIG. 2) and an optical unit 51 (FIG. 3), which will be described later. The distal end portion 21 is provided with an observation window (not illustrated), and light from an object is incident on a light receiving surface of the image pickup device 34 through the observation window and an image pickup optical system 35 (FIG. 2) of the optical unit 51. The image pickup optical system 35 is an observation optical system that has a focusing control mechanism. An image pickup signal obtained by the image pickup device 34 is supplied to the video processor 3 via a signal line inserted into the insertion section 11, the operation section 12, and the universal cable 13.

Note that various signal lines configured to deliver drive signals for a voice coil motor 32 (FIG. 2) and a sensor section 33 (FIG. 2), which will be described later, a position detection signal from the sensor section 33, and the like are also inserted into the universal cable 13.

Further, an illumination window (not illustrated) is also provided at the distal end portion 21. Illumination light is emitted from the illumination window.

A user of the endoscope apparatus 1 can bend the bending section 22 in a desired direction by operating a bending knob 24 provided at the operation section 12.

Various operation devices such as a release button are provided at the operation section 12. A connector 14 is provided at a distal end of the universal cable 13 extending from the operation section 12. The connector 14 is adapted to be able to be detachably attached to the video processor 3.

The video processor 3 includes a light source device including a light source such as a lamp configured to generate illumination light, and the illumination light is incident on a proximal end surface of an optical fiber (not illustrated) inserted into the insertion section 11, the operation section 12, and the universal cable 13 and is then emitted from a distal end surface of the optical fiber disposed in the distal end portion 21 of the insertion section 11. The illumination light emitted from the distal end surface of the optical fiber is emitted from the illumination window.

Note that the illumination light may be light of a light emitting element such as a light emitting diode (LED) incorporated in the distal end portion 21.

The video processor 3 incorporates a control section configured to control the entire endoscope apparatus 1. The user can perform various operations using various buttons of the operation section 12, an operation panel 3a of the video processor 3, and the like. The video processor 3 executes programs in accordance with various functions in response to operations performed by the user.

The video processor 3 is a processor, to which an image pickup signal is inputted from the endoscope 2 to generate an endoscope image that is a subject image. An image signal of the endoscope image is outputted to the monitor 4, and the endoscope image is displayed on the monitor 4.

The video processor 3 has a focal point control section 46 (FIG. 2) that controls a focusing position of a lens for focusing control of the image pickup optical system based on the endoscope image generated using the image pickup signal from the image pickup device 34 or based on a distance measurement signal included in the image pickup device 34.

As described above, the endoscope apparatus 1 includes the endoscope 2 having an observation optical system having a lens driving mechanism and the video processor 3 that is a processor to which the endoscope 2 is connected.

Figure 2:
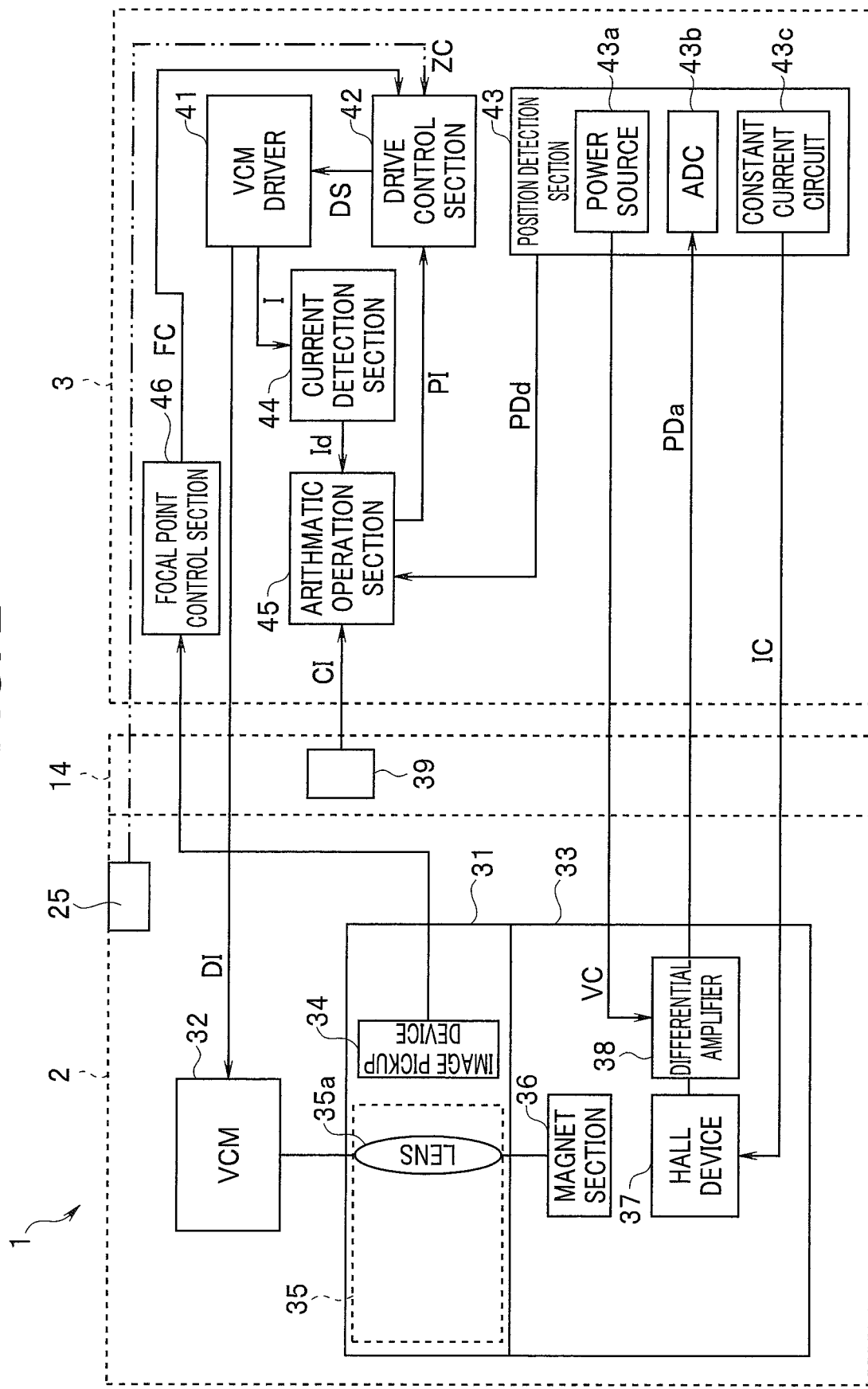
FIG. 2 is a block diagram illustrating the configuration of the endoscope apparatus 1 according to the embodiment of the invention.

FIG. 2 is a block diagram illustrating a configuration of the endoscope apparatus 1.

The endoscope 2 has an image pickup section 31, the voice coil motor (VCM) 32 that serves as an actuator, and the sensor section 33. The image pickup section 31, the voice coil motor 32, and the sensor section 33 are provided in the distal end portion 21 of the insertion section 11.

The image pickup section 31 has the image pickup device 34 such as a CCD image sensor and the image pickup optical system 35. The image pickup optical system 35 is an optical system including a plurality of lenses and capable of adjusting a focus position and includes a lens 35a that is a movable lens. Although FIG. 2 illustrates only one lens 35a in the image pickup optical system 35, a plurality of movable lenses may be provided.

The image pickup device 34 receives light of an object image using a light receiving surface through the image pickup optical system 35, performs photoelectric conversion, and outputs an image pickup signal to the video processor 3. The image pickup optical system 35, the voice coil motor 32, and the sensor section 33 are disposed at an optical unit 51 (FIG. 3) in the distal end portion 21. A configuration of the optical unit 51 will be described later.

The voice coil motor 32 is an actuator provided in the endoscope 2 and configured to drive lenses related to the lens driving mechanism. Here, the voice coil motor 32 is provided in the distal end portion 21 and moves the lens 35a along an optical axis of the image pickup optical system 35. The voice coil motor 32 is an electric actuator that is configured to include one or more coils and one or more magnets and that is driven by a drive current DI from the video processor 3.

The voice coil motor 32 is of a so-called moving magnet type and has a structure in which the magnet is movable with respect to the coil.

The lens 35a is fixed to a movable section 53 (FIG. 3) on which a magnet section 36 (FIG. 3) of the voice coil motor 32 is mounted. The lens 35a can be moved in the optical axis direction of the image pickup optical system 35 by the voice coil motor 32 relatively moving the movable section 53 with respect to a coil section 101 (FIG. 3) in the voice coil motor 32. In other words, the voice coil motor 32 is of a moving magnet type that is provided in the endoscope 2 and has the magnet section 36 and the coil section 101 such that the magnet section 36 is movable with respect to the coil section 101.

As described above, the voice coil motor 32 provided at the distal end portion 21 is an actuator that has the magnet section 36 (FIG. 3) having one or more magnets and the coil section 101 (FIG. 3) having one or more coils and that is capable of relatively moving the movable section 53 with respect to the coil section 101.

Note that although the magnet section 36 is illustrated in the sensor section 33 in FIG. 2, the magnet section 36 is a part of the voice coil motor 32.

The sensor section 33 is a sensor provided in the endoscope 2 and configured to detect the position of the lens 35a related to a focus adjusting mechanism. Specifically, the sensor section 33 is configured to have a Hall device 37 and a differential amplifier 38. The magnet section 36 includes eight magnets as will be described later. The magnet section 36 that configures the voice coil motor 32 is connected and fixed to the lens 35a, and the magnet section 36 moves along with the lens 35a.

The Hall device 37 is a sensor configured to be driven by a drive current IC from a constant current circuit 43c, which will be described later, and detect a magnetic field of the magnet section 36. The Hall device 37 that is a magnetic sensor is disposed in the vicinity of the coil section 101 and detects the magnetic field of the magnet section 36 in order to detect the position of the magnet section 36.

The Hall device 37 outputs an analog signal in accordance with a magnitude of the detected magnetic field. Since the magnitude of the detected magnetic field changes in accordance with the position of the magnet section 36, an outputted voltage of the Hall device 37 indicates the position of the magnet section 36. Note that the sensor for position detection may be a magnetoresistive element instead of the Hall device 37.

As described above, the sensor section 33 has the Hall device or the magnetoresistive element configured to detect a change in the magnetic field that accompanies movement of the lens 35a for focusing control, and the Hall device or the magnetoresistive element receives supply of the drive current IC, which is a constant current, from the constant current circuit 43c.

The differential amplifier 38 amplifies the analog signal from the Hall device 37 and outputs a sensor output signal PDa that is a voltage signal. In other words, the sensor section 33 outputs the sensor output signal PDa in accordance with the position of the lens 35a driven by the voice coil motor 32.

Figure 3:
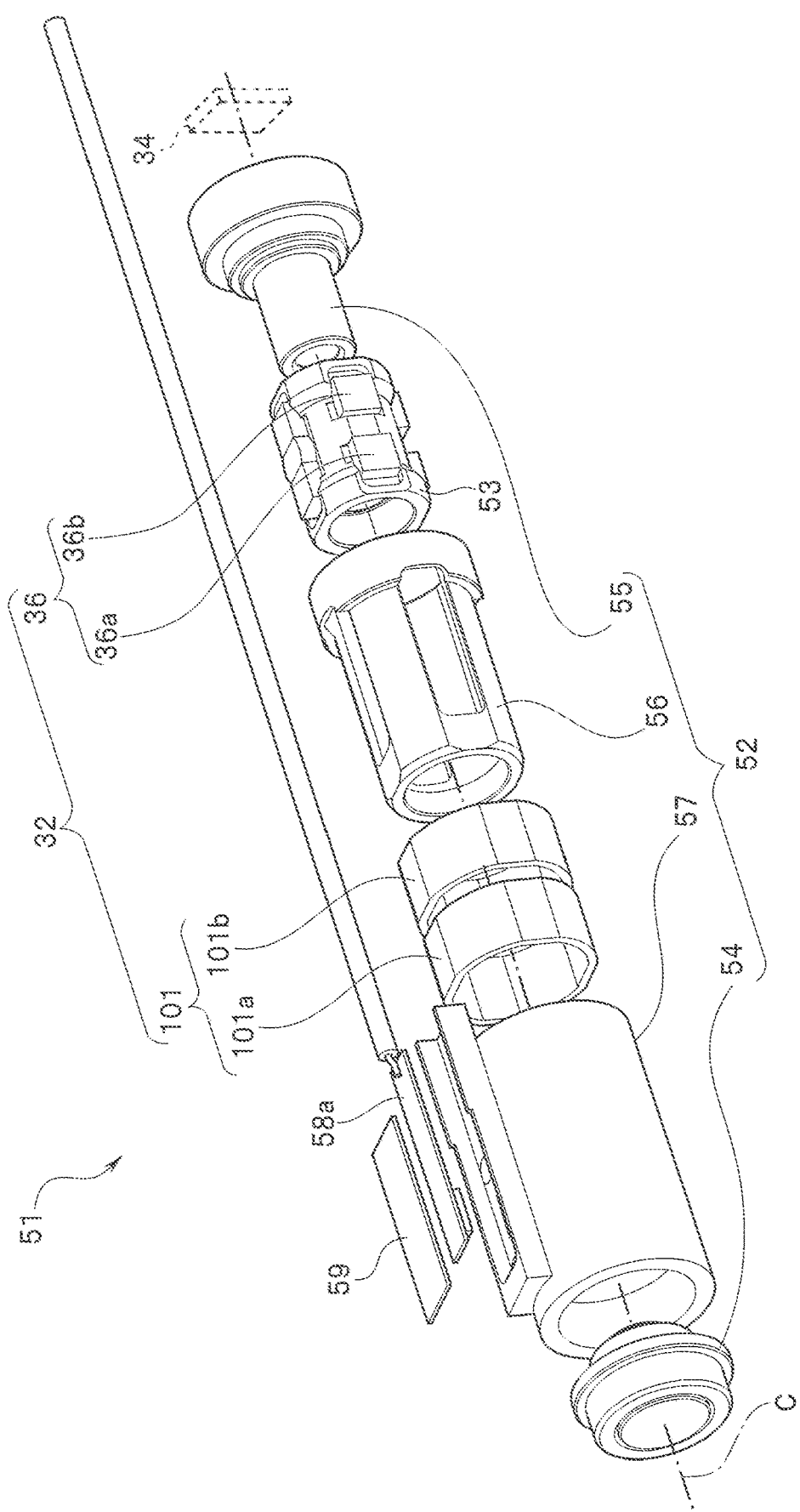
FIG. 3 is an exploded perspective view illustrating a configuration of an optical unit 51 disposed at a distal end portion 21 of an insertion section 11 of an endoscope 2 according to the embodiment of the invention.

The voice coil motor 32, the sensor section 33, the image pickup optical system 35, the Hall device 37, and the differential amplifier 38 are included in the optical unit 51 (FIG. 3).

The connector 14 of the universal cable 13 of the endoscope 2 incorporates a nonvolatile and rewritable memory 39. The memory 39 stores correction information CI. The correction information CI is information for correcting influences of a magnetic field due to a magnetic flux leaking from the voice coil motor 32 in the sensor output signal PDa of the sensor section 33. Since detection properties of the sensor section 33 vary for each endoscope due to component properties of the voice coil motor 32, assembly errors, and the like, the correction information CI is information for cancelling the amount of error due to the leaking magnetic flux included in the sensor output signal PDa and is stored as individual information of the endoscope 2 in the memory 39 of the endoscope 2.

Specifically, the correction information CI is used by an arithmetic operation section 45, which will be described later, in order to correct the position of the magnet section 36 detected by the sensor section 33. The memory 39 is a nonvolatile and rewritable memory such as a flash memory. Here, the memory 39 stores information regarding correction coefficients corresponding to coil currents as the correction information CI when the endoscope 2 is manufactured. The correction coefficients corresponding to coil currents are determined based on data actually measured for each endoscope.

When the endoscope 2 is connected to the video processor 3, the correction information CI recorded in the memory 39 is read by the video processor 3.

The video processor 3 has a voice coil motor (VCM) driver 41, a drive control section 42, a position detection section 43, a current detection section 44, the arithmetic operation section 45, and the focal point control section 46.

The video processor 3 has the control section (not illustrated) as described above. The control section includes a central processing unit (CPU), a ROM, a RAM, and the like and controls driving of the voice coil motor 32 in addition to overall operations of the endoscope apparatus 1, generation of various images, and various kinds of processing in accordance with various functions. Programs for various kinds of processing are performed by executing programs stored in the ROM. FIG. 2 illustrates only a plurality of blocks related to the control of driving of the voice coil motor 32.

The voice coil motor driver 41 is a circuit configured to generate the drive current DI for the voice coil motor 32, output the drive current DI to the voice coil motor 32, and also supply a current signal I indicating a current value of a current to be supplied to the voice coil motor 32 to the current detection section 44.

The drive control section 42 is a circuit configured to generate a driving command signal DS and output the driving command signal DS to the voice coil motor driver 41 based on a focusing position command signal FC from the focal point control section 46 and lens position information PI from the arithmetic operation section 45. Specifically, the drive control section 42 performs feedback control of the focusing position based on the lens position information PI from the arithmetic operation section 45 such that the lens 35a is located at a focusing position designated through a command using the focusing position command signal FC, generates the driving command signal DS as a control signal, and outputs the driving command signal DS to the voice coil motor driver 41.

The position detection section 43 is a position detection circuit including a power source 43a, an analog-to-digital converter (hereinafter, abbreviated as an ADC) 43b, and the constant current circuit 43c.

The power source 43a is a circuit configured to supply a power source voltage VC to the differential amplifier 38 via a signal line.

The ADC 43b converts the sensor output signal PDa that is an analog output from the differential amplifier 38 into a sensor output signal PDd that is a digital signal. The sensor output signal PDd indicates the position of the lens 35a.

The constant current circuit 43c is a circuit configured to supply the drive current IC, which is a constant current, to the Hall device 37 via a signal line.

The current detection section 44 is a circuit configured to detect the drive current DI outputted by the voice coil motor driver 41. Specifically, the current signal I that is proportional to the drive current DI outputted by the voice coil motor driver 41 is inputted to the current detection section 44, and the current detection section 44 outputs a digital current signal Id to the arithmetic operation section 45.

The arithmetic operation section 45 is a circuit, into which the sensor output signal PDd from the position detection section 43 and the digital current signal Id from the current detection section 44 are inputted, which outputs the lens position information PI to the drive control section 42.

Configurations of the position detection section 43, the current detection section 44, and the arithmetic operation section 45 will be described later.

The focal point control section 46 outputs the focusing position command signal FC for controlling the focusing position of the lens 35a for the focusing control in the image pickup optical system based on the endoscope image generated from the image pickup signal from the image pickup device 34 or based on the distance measurement signal included in the image pickup device 34 as described above.

Next, a configuration of the optical unit disposed in the distal end portion 21 will be described.

Figure 4:
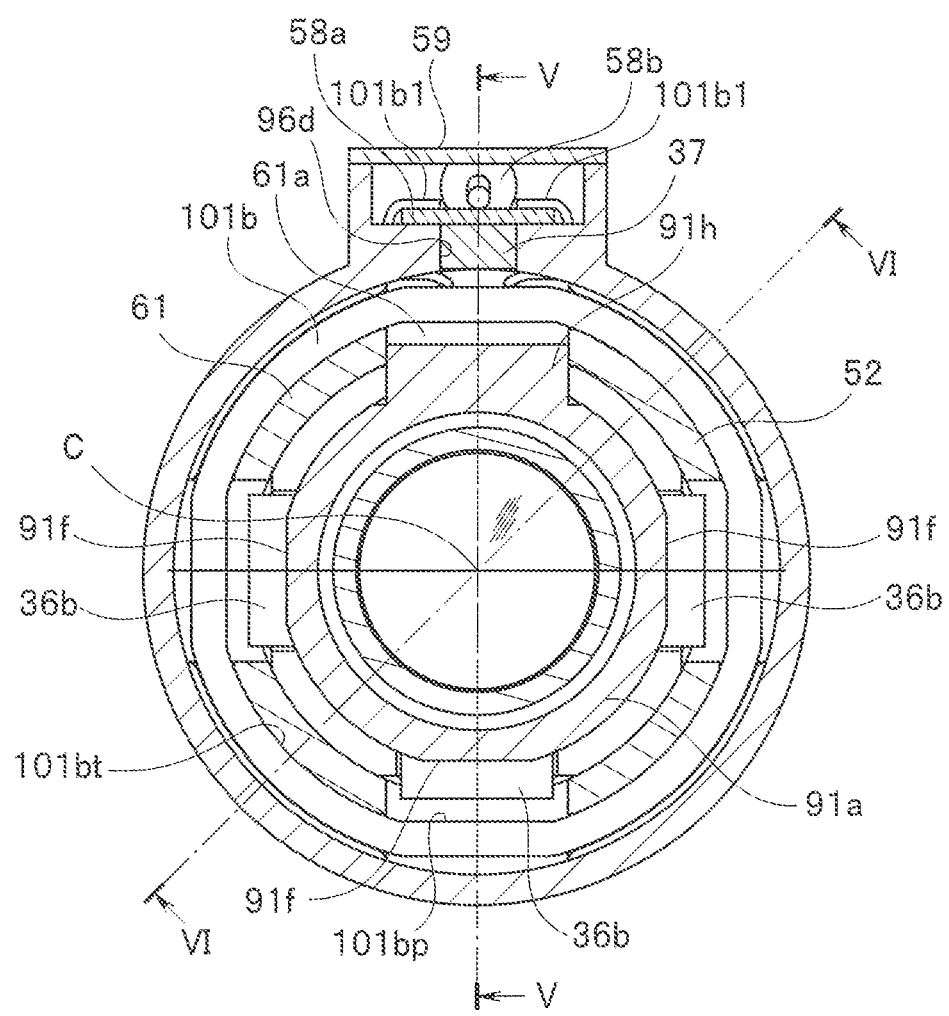
FIG. 4 is a sectional view illustrating a configuration of main components in the optical unit 51 according to the embodiment.

FIG. 3 is an exploded perspective view illustrating a configuration of the optical unit 51 disposed at the distal end portion 21 of the insertion section 11 of the endoscope 2 according to the embodiment of the invention. FIG. 4 is a sectional view illustrating a configuration of main components in the optical unit 51 according to the embodiment.

Figure 5:
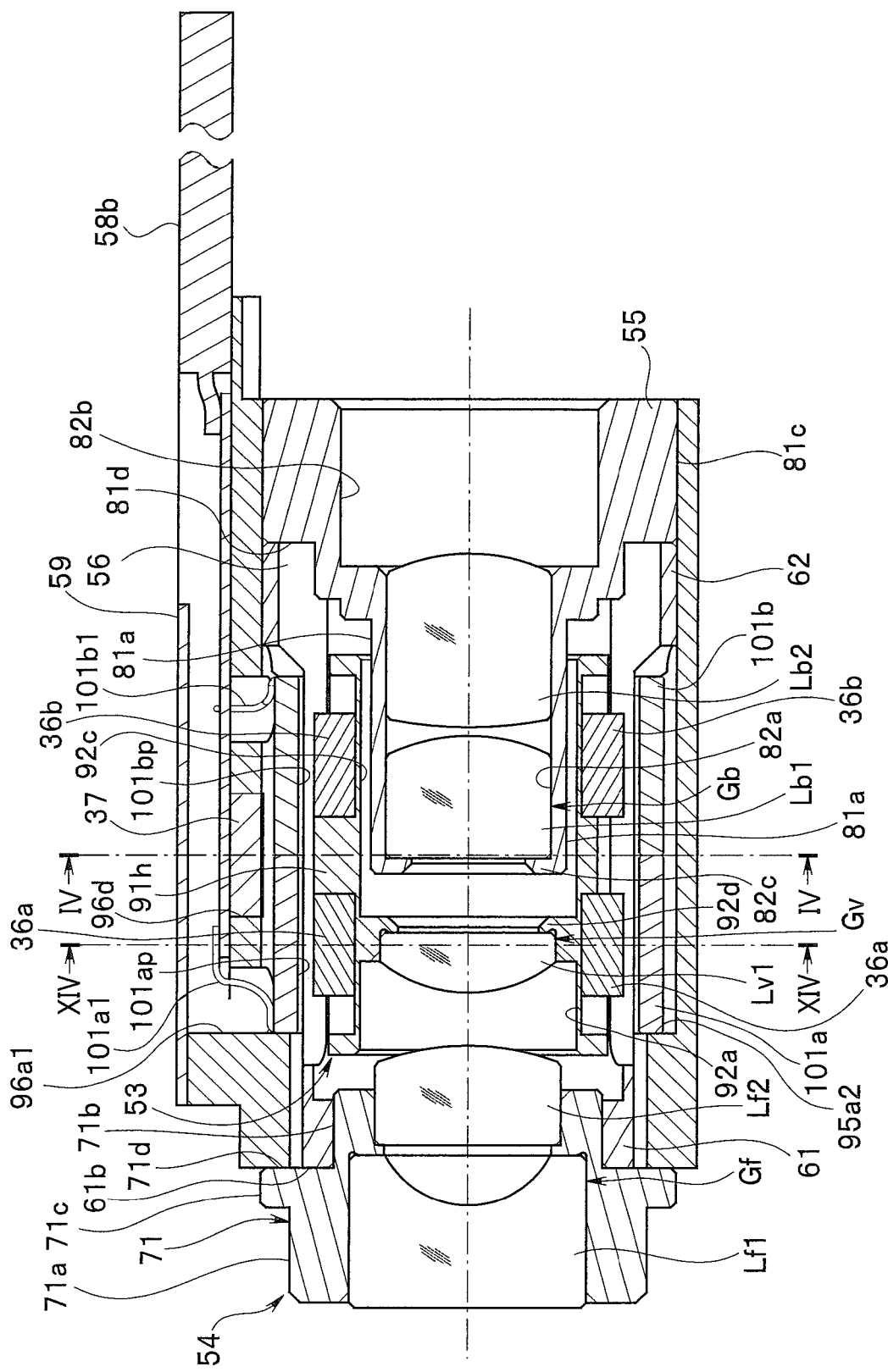
FIG. 5 is a sectional view of the optical unit 51 when seen in a cut plane passing through the line V-V in FIG. 4.
Figure 6:
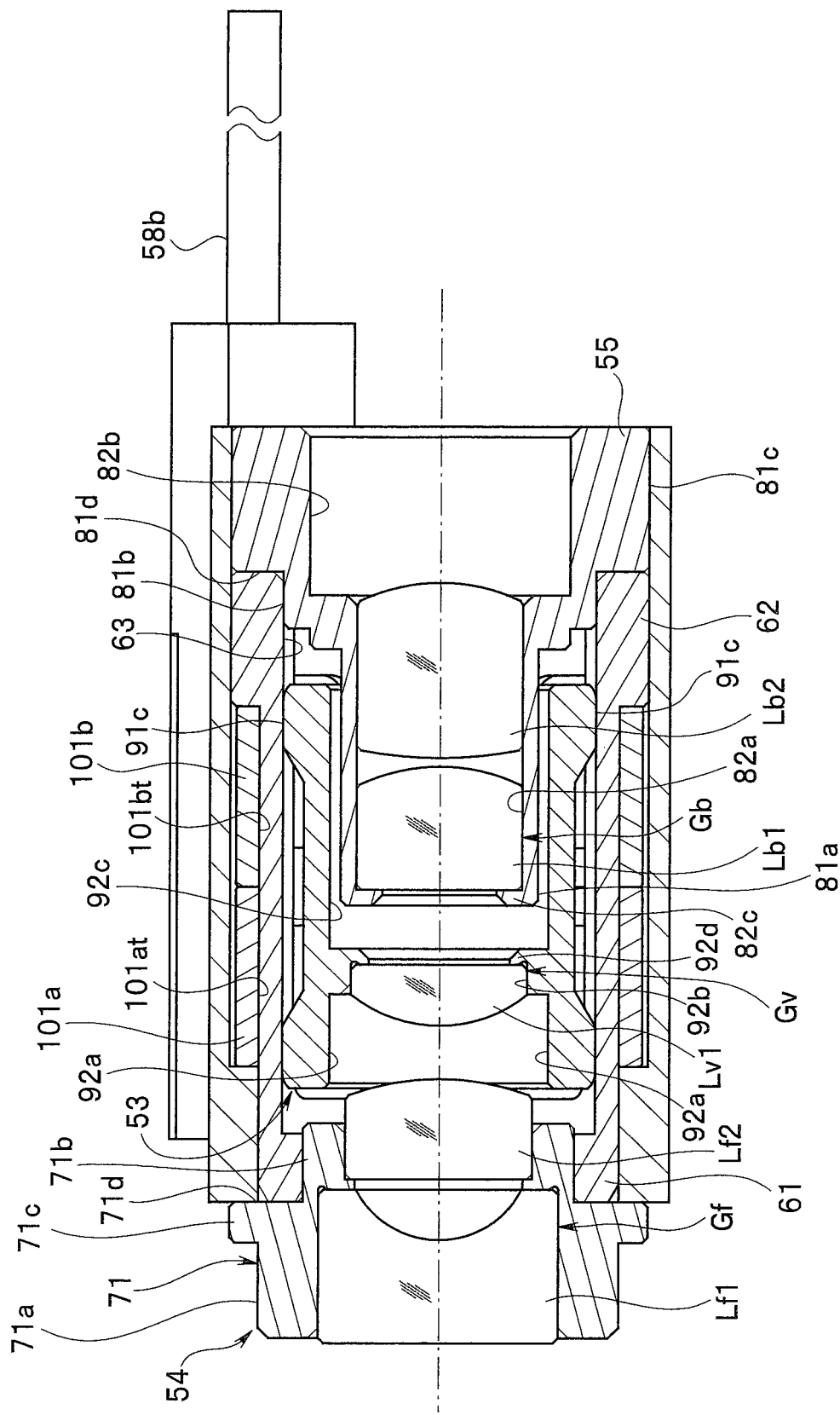
FIG. 6 is a sectional view of the optical unit 51 when seen in a cut plane passing through the line VI-VI in FIG. 4.

FIG. 5 is a sectional view of the optical unit 51 when seen in a cut plane passing through the line V-V in FIG. 4. FIG. 6 is a sectional view of the optical unit 51 when seen in a cut plane passing through the line VI-VI in FIG. 4. Note that FIG. 4 is also a sectional view of the optical unit 51 when seen in a cut plane passing through the line IV-IV in FIG. 5.

The optical unit 51 illustrated in FIGS. 3 to 6 includes a fixed section 52, the movable section 53 that is movable with respect to the fixed section 52, and the voice coil motor 32 that generates a drive force for causing the movable section 53 to move with respect to the fixed section 52.

Hereinafter, a configuration of each component in the optical unit 51 will be described.
(Configuration of Fixed Section 52)

The fixed section 52 has a front frame section 54, a rear frame section 55, a fixed section main body 56, and a sensor section fixed section 57. The sensor section 33 is provided so as to be fixed to the sensor section fixed section 57. As illustrated in FIGS. 5 and 6, the front frame section 54 holds an object-side fixed lens group Gf on a side closer to an object than a movable lens group Gv held by the movable section 53 and is attached to the fixed section main body 56 on the side of the object. The rear frame section 55 holds an image-side fixed lens group Gb on a side closer to an image than the movable lens group Gv and is attached to the fixed section main body 56 on the side of the image. Hereinafter, the side opposite to the side of the object along an axis C will be referred to as a side of the image.

First, a configuration of the fixed section main body 56 will be described.
(Configuration of Fixed Section Main Body 56)

Figure 7:
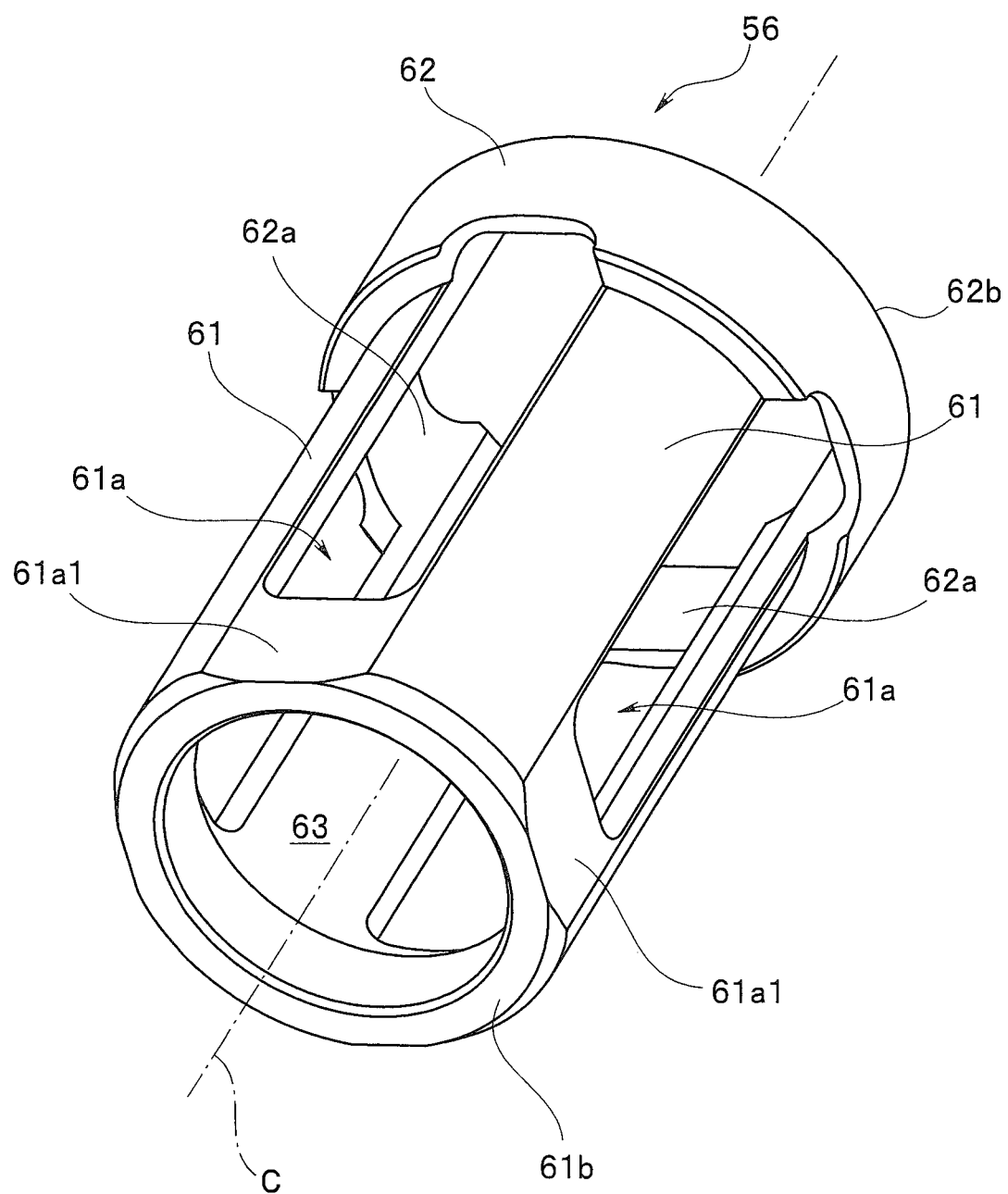
FIG. 7 is a perspective view illustrating a configuration of a fixed section main body 56 according to the embodiment.

FIG. 7 is a perspective view illustrating a configuration of the fixed section main body 56. The fixed section main body 56 illustrated in the drawing is a tubular-shaped member around a predetermined axis C. The fixed section main body 56 has a tubular section 61 having the axis C as a central axis and an image-side thick section 62 formed on the side of the image with respect to the tubular section 61. The fixed section main body 56 has rotation symmetricity of 90° with respect to the axis C.

In the tubular section 61, four punched sections 61a are formed. Specifically, the four punched sections 61a respectively penetrating through the tubular section 61 in the radial direction are formed at every 90° in the circumferential direction with respect to the central axis C in the longitudinal direction of the tubular section 61. The respective punched sections 61a are formed in plane sections 61a1 formed on an outer circumferential surface of the tubular section 61 parallel to the central axis C. The four plane sections 61a1 are also provided at every 90° in the circumferential direction with respect to the central axis C in the longitudinal direction of the tubular section 61.

A surface inside the tubular section 61 in the radial direction except for the four punched sections 61a is a tubular-shaped cylindrical surface and serves as a fixed-side sliding surface 63 configured to support and guide the movable section 53. The fixed-side sliding surface 63 has a shape divided in the circumferential direction with the four punched sections 61a.

The coil section 101 of the voice coil motor 32 is fixed to the outer circumferential portion of the tubular section 61 as illustrated in FIGS. 4 to 6. Thus, the coil section 101 is fixed to the fixed section 52.

The image-side thick section 62 is formed so as to project outward beyond the tubular section 61 in the radial direction. In the fixed-side sliding surface 63 inside the image-side thick section 62 in the radial direction, four grooves 62a are formed. When the movable section 53 is assembled, plurality of magnets of the magnet section 36, which will be described later, pass through the four grooves 62a. Therefore, it is possible to smoothly assemble the movable section 53 with the fixed section main body 56. Note that a structure in which the image-side thick section 62 is formed separately from the tubular section 61 and is attached to the tubular section 61 at the time of assembly may also be employed.

Next, a configuration of the front frame section 54 will be described.
(Configuration of Front Frame Section 54)

Figure 8A:
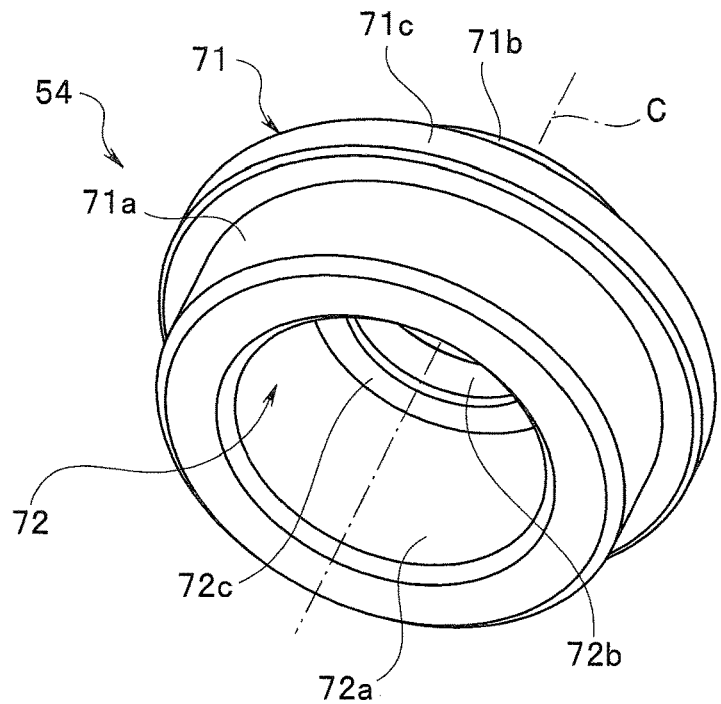
FIG. 8A is a perspective view illustrating a configuration of a front frame section 54 according to the embodiment.
Figure 8B:
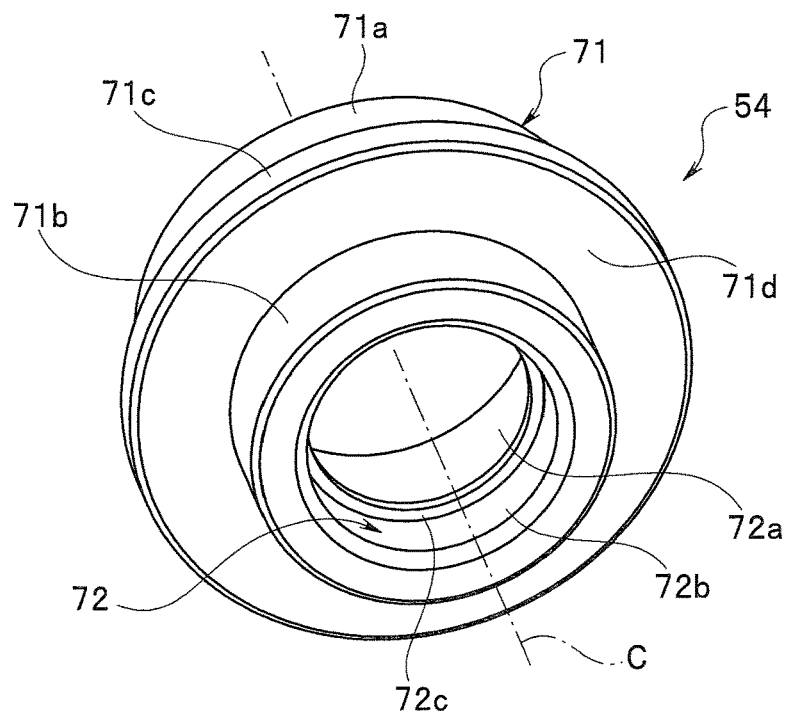
FIG. 8B is a perspective view illustrating the configuration of the front frame section 54 according to the embodiment.

FIGS. 8A and 8B are perspective views illustrating a configuration of the front frame section 54 and perspective views when seen from different sides of the axis C, respectively. Note that the central axis of the front frame section 54 is referred to as the axis C because the central axis coincides with the central axis of the fixed section main body 56 at the time of assembly.

The front frame section 54 is a tubular-shaped member that has an outer circumferential portion 71 and an inner circumferential portion 72. The outer circumferential portion 71 has a first outer circumferential portion 71a, a second outer circumferential portion 71b, and an outer circumference-side projecting portion 71c. The inner circumferential portion 72 has a first inner circumferential portion 72a, a second inner circumferential portion 72b, and an inner circumference-side projecting portion 72c.

In the outer circumferential portion 71, the diameter of the first outer circumferential portion 71a is larger than the diameter of the second outer circumferential portion 71b. The outer circumference-side projecting portion 71c with the largest diameter projecting outward in the radial direction is provided between the first outer circumferential portion 71 and the second outer circumferential portion 71b.

In the inner circumferential portion 72, the diameter of the first inner circumferential portion 72a is larger than the diameter of the second inner circumferential portion 72b. The inner circumference-side projecting portion 72c with the smallest diameter projecting inward in the radial direction is located between the first inner circumferential portion 72a and the second inner circumferential portion 72b.

The front frame section 54 holds the object-side fixed lens group Gf. The object-side fixed lens group Gf has a first front lens Lf1 and a second front lens Lf2 aligned in this order from the side of the object. The first inner circumferential portion 72a holds the first front lens Lf1, and the second inner circumferential portion 72b holds the second front lens Lf2. An image-side outer edge portion of the first front lens Lf1 and an object-side outer edge portion of the second front lens Lf2 preferably abut on the inner circumference-side projecting portion 72c as illustrated in FIGS. 5 and 6.

When the front frame section 54 is inserted into the fixed section main body 56, the front frame section 54 is inserted until an end surface 61b of the fixed section main body 56 on the side of the object comes into contact with a step portion 71d between the second outer circumferential portion 71b and the outer circumference-side projecting portion 71c while the second outer circumferential portion 71b is brought into contact with the fixed-side sliding surface 63 of the tubular section 61 of the fixed section main body 56. In this manner, the front frame section 54 is inserted into the fixed section main body 56 and is fixed to the fixed section main body 56 with an adhesive or the like.

Next, a configuration of the rear frame section 55 will be described.

(Configuration of Rear Frame Section 55)

Figure 9A:
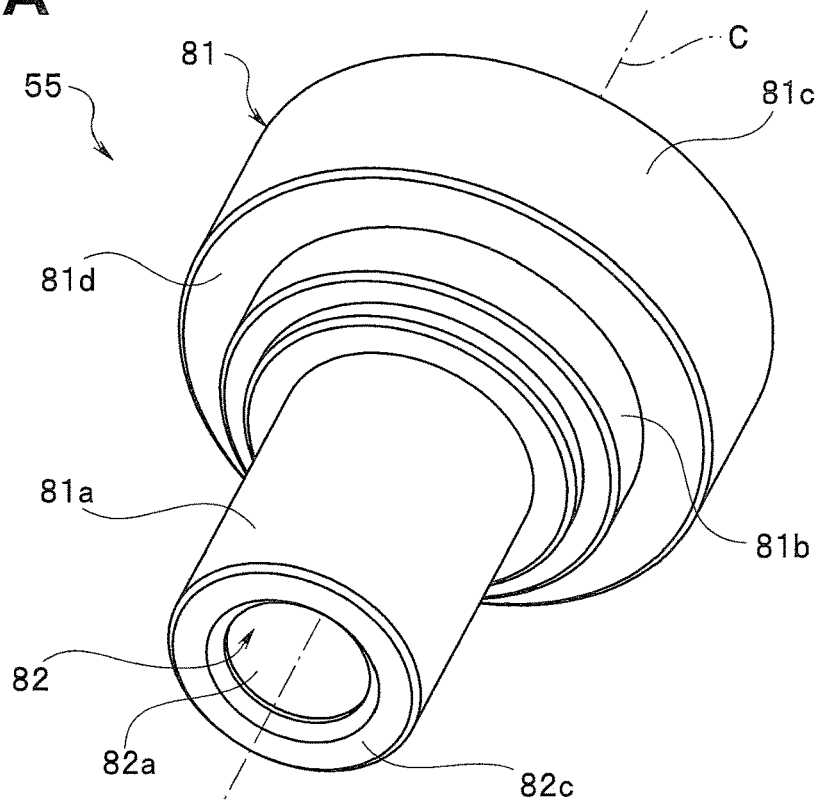
FIG. 9A is a perspective view illustrating a configuration of a rear frame section 55 according to the embodiment.
Figure 9B:
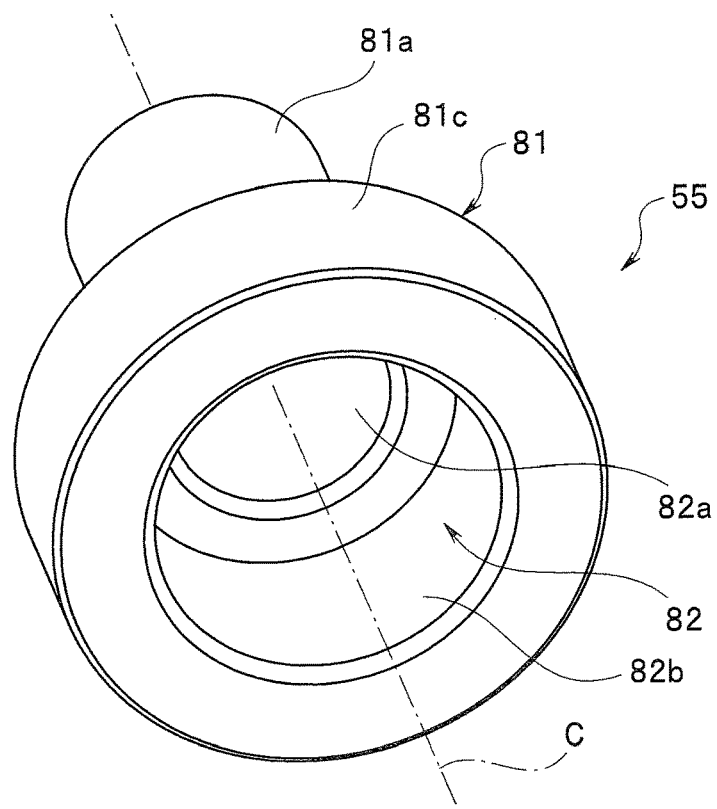
FIG. 9B is a perspective view illustrating the configuration of the rear frame section 55 according to the embodiment.

FIGS. 9A and 9B are perspective views illustrating a configuration of the rear frame section 55 and perspective views when seen from different sides of the axis C, respectively. Note that the central axis of the rear frame section 55 is referred to as the axis C because the central axis coincides with the central axis of the fixed section main body 56 at the time of assembly similarly to the front frame section 54. The rear frame section 55 is a tubular-shaped member that has an outer circumferential portion 81 and an inner circumferential portion 82. The outer circumferential portion 81 has a first outer circumferential portion 81a, a second outer circumferential portion 81b, and a third outer circumferential portion 81c. The inner circumferential portion 82 has a first inner circumferential portion 82a, a second inner circumferential portion 82b, and an inner circumference-side projecting portion 82c.

In the outer circumferential portion 81, the diameter of the first outer circumferential portion 81a is smaller than the diameter of the second outer circumferential portion 81b, and the diameter of the second outer circumferential portion 81b is smaller than the diameter of the third outer circumferential portion 81c.

In the inner circumferential portion 82, the diameter of the first inner circumferential portion 82a is smaller than the diameter of the second inner circumferential portion 82b. The inner circumference-side projecting portion 82c with the smallest diameter projecting inward in the radial direction is provided at an end portion of the first inner circumferential portion 82a on the side of the object.

The rear frame section 55 holds the image-side fixed lens group Gb. The image-side fixed lens group Gb has a first rear lens Lb1 and a second rear lens Lb2. The first inner circumferential portion 82a holds the first rear lens Lb1 and the second rear lens Lb in this order from the side of the object. The first rear lens Lb1 on the side of the object preferably abuts on the inner circumference-side projecting portion 82c as illustrated in FIGS. 5 and 6.

When the rear frame section 55 is inserted into the fixed section main body 56, the rear frame section 55 is inserted until an end surface 62b of the fixed section main body 56 on the side of the image comes into contact with a step portion 81d between the second outer circumferential portion 81b and the third outer circumferential portion 81c while the second outer circumferential portion 81b is brought into contact with the fixed-side sliding surface 63 of the image-side thick section 62 of the fixed section main body 56.

Next, a configuration of the sensor section fixed section 57 that is a sensor fixed member will be described.
(Configuration of Sensor Section Fixed Section 57)

Figure 10:
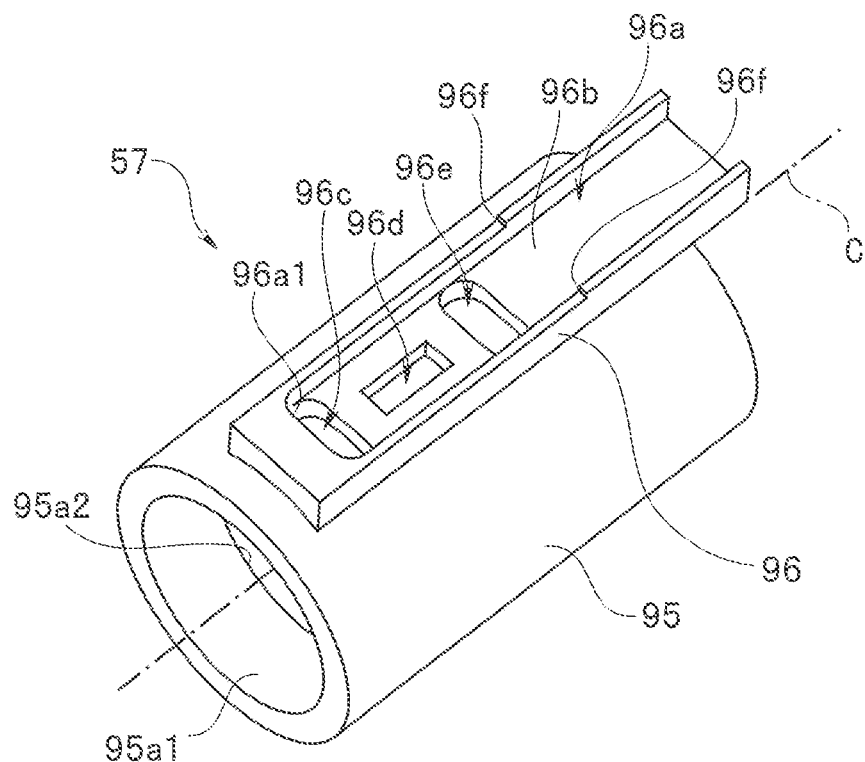
FIG. 10 is a perspective view illustrating a configuration of a sensor section fixed section 57 according to the embodiment.

FIG. 10 is a perspective view illustrating a configuration of the sensor section fixed section 57. The sensor section fixed section 57 illustrated in the drawing is a tubular-shaped member around the predetermined axis C. The sensor section fixed section 57 has a tubular section 95 around the axis C as the central axis and a sensor mounting section 96 projecting in the outer diameter direction from the outer circumferential surface of the tubular section 95.

The sensor section fixed section 57 has a tubular shape into which the fixed section main body 56 is inserted along the central axis C. The tubular section 95 and the sensor mounting section 96 are integrally formed.

A step portion 95a2 on which the coil section 101 abuts when the coil section 101 of the voice coil motor 32 is inserted into the tubular section 95 from the side of the image is formed in an inner circumferential surface 95a1 of the tubular section 95.

The sensor mounting section 96 has a rectangular parallelepiped shape and has an elongated groove section 96a formed along the axis C and opened in the outer diameter direction of the tubular section 95. The groove section 96a has a shape with a wall section 96a1 on the side of the object and with no wall section on the side of the image.

Three holes 96c, 96d, and 96e are formed in a bottom portion 96b of the elongated groove section 96a in this order from the side of the object.

The sensor section 33 is mounted in and fixed to the groove section 96a of the sensor mounting section 96.

Next, a configuration of the sensor section 33 will be described.
(Configuration of Sensor Section 33)

Figure 11:
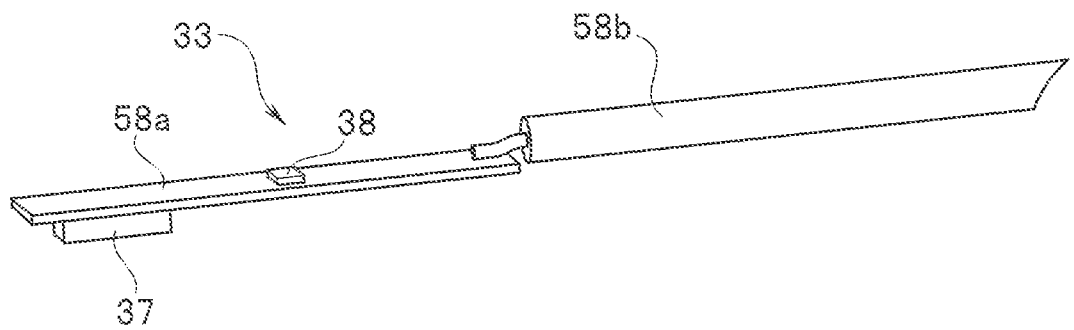
FIG. 11 is a perspective view of a sensor section 33 according to the embodiment.

FIG. 11 is a perspective view of the sensor section 33.

The sensor section 33 includes the Hall device 37 that serves as a magnetic sensor and a circuit board 58a on which the Hall device 37 is mounted. The differential amplifier 38 is also mounted on the circuit board 58a. The circuit board 58a is disposed in the groove section 96a of the sensor mounting section 96 and has an elongated shape with which the circuit board 58a can be fixed to the bottom portion 96b.

The circuit board 58a is fixed to the inside of the groove section 96a with an adhesive or the like such that the Hall device 37 enters the hole 96d. The position of the hole 96d defines the position of the Hall device 37. In other words, the hole 96d is a hole for positioning the Hall device 37.

As illustrated in FIG. 4, the hole 96d is formed at a position that faces magnets 36a and 36b of the magnet section 36 of the movable section 53 when the optical unit 51 is seen along the axis C from the side of the object.

Although a configuration of the movable section 53 will be described later, the movable section 53 has the magnet section 36 of the voice coil motor 32 and moves forward and backward in the axis C direction. The hole 96d is formed such that, in defining the position of the end surface of the magnet section 36 on the side of the object when the movable section 53 moves closest to the side of the object as P1 and the position of the end surface of the magnet section 36 on the side of the image when the movable section 53 moves closest to the side of the image as P2, the Hall device 37 is located within a range M between the positions P1 and P2 in the axis C direction.

Figure 12:
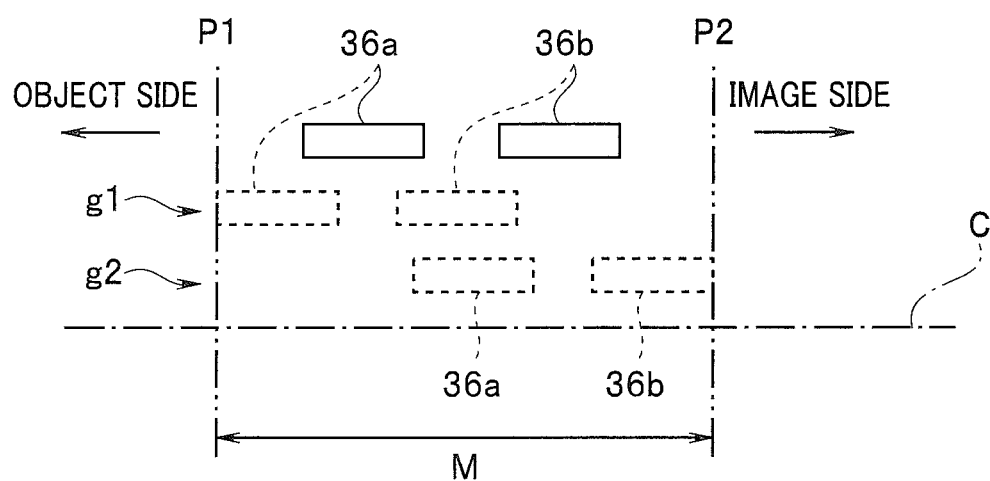
FIG. 12 is a diagram for explaining a moving range of a magnet section 36 according to the embodiment.

FIG. 12 is a diagram for explaining a moving range of the magnet section 36. The magnet section 36 has the plurality of magnets 36a and 36b as will be described later. In FIG. 12, g1 represents the position of the magnet section 36 when the magnets 36a and 36b of the magnet section 36 have moved closest to the side of the object. Likewise, g2 represents the position of the magnet section 36 when the magnets 36a and 36b of the magnet section 36 have moved closest to the side of the image. The hole 96d is formed such that the Hall device 37 is located within the range M between the position P1 and the position P2 in the axis C direction.

In other words, the Hall device 37 that is a magnetic sensor is located between the end surface of the magnet section 36 on the side in the moving direction of the magnet 36a when the magnet section 36 has moved in the direction on the side of the object along the central axis C and the end surface of the magnet section 36 on the side in the moving direction of the magnet 36b when the magnet section 36 has moved in the direction on the side of the image, which is a direction opposite to the direction on the side of the object, along the central axis C.

Each of the holes 96c and 96e is a hole for coil wires. The coil wires are electric wires for the coil of the coil section 101. The hole 96c is a hole for extracting two coil wires (not illustrated) of a first coil 101a of the coil section 101, which will be described later, from the inside to the outside of the tubular section 95 as illustrated in FIG. 5. The hole 96e is a hole for extracting two coil wires 101b1 (FIGS. 4 and 5) of second coil 101b of the coil section 101, which will be described later, from the inside to the outside of the tubular section 95.

As described above, the coil section 101 is disposed at an outer circumferential portion of the fixed section main body 56. Since the fixed section main body 56 is disposed inside the sensor section fixed section 57, the coil section 101 is disposed inside the sensor section fixed section 57. The holes 96c and 96e for allowing the coil wires of the coil section 101 to pass are formed in the sensor section fixed section 57.

The two coil wires 101a1 of the first coil 101a and the two coil wires 101b1 of the second coil 101b are connected to a wiring pattern for a coil current line on the circuit board 58a. The Hall device 37 and a wiring pattern of the differential amplifier 38 are also provided independently from the coil current line on the circuit board 58a.

A distal end of a signal cable 58b is soldered at an end of the circuit board 58a on the side of the image. The signal cable 58b is inserted into the insertion section 11 of the endoscope 2.

An elongated urging plate 59 is provided so as to cover the groove section 96a of the sensor mounting section 96 as illustrated in FIGS. 3 and 5. The urging plate 59 is a rectangular plate-shaped magnetic body and is, for example, a cold rolled steel plate.

A step portion 96f for positioning the urging plate 59 is formed at a peripheral portion of the groove section 96a of the sensor mounting section 96 on a side of the opening. The step portion 96f is formed such that the distance from the axis C to the peripheral portion of the groove section 96a on the side of the opening is shorter on the side of the object than on the side of the image. The urging plate 59 is fixed to the sensor mounting section 96 with an adhesive or the like such that an end on the side of the image abuts on the step portion 96f and covers the groove section 96a.

The length of the urging plate 59 in the axis C direction is equal to or greater than the aforementioned range M between the positions P1 and P2, and the urging plate 59 is disposed to include the range between the positions P1 and P2 in the axis C direction when the urging plate 59 is fixed to the sensor mounting section 96.

The magnets 36a and 36b of the movable section 53 are constantly equally attracted toward the side of the urging plate 59 by providing the urging plate 59 in this manner.

In other words, the urging plate 59 as an urging member that is a magnetic body is provided at the sensor section fixed section 57, and the urging plate 59 is disposed at the sensor section fixed section 57 so as to attract the magnet section 36 in the outer diameter direction of the sensor section fixed section 57.

Even if there is a gap between the inner circumferential surface of the fixed section main body 56 and the outer surface of the magnet section 36 of the movable section 53 in the fixed section main body 56 of the fixed section 52, an increase in inclination of the movable section 53 with respect to the axis C is curbed since the magnets 36a and 36b are attracted to the urging plate 59.

Motion of the movable section 53 along the axis C is stabilized, and it is also possible to prevent degradation of accuracy of position detection performed by the sensor section 33, by providing such an urging plate 59.

Since the urging plate 59 functions as a yoke of the magnet section 36, there is also an effect of increasing a magnetic force of the magnet section 36. As a result, it is possible to increase the outputted signal of the Hall device 37, and an effect that accuracy of position detection can be improved is also achieved.

The respective components of the fixed section 52 with the aforementioned configuration are configured using materials that are non-magnetic bodies but have relative magnetic permeability of greater than 1.0, for example. Examples of such materials include austenite-based stainless steel.

Next, a configuration of the movable section 53 that is a movable member will be described.

(Configuration of Movable Section 53)

Figure 13:
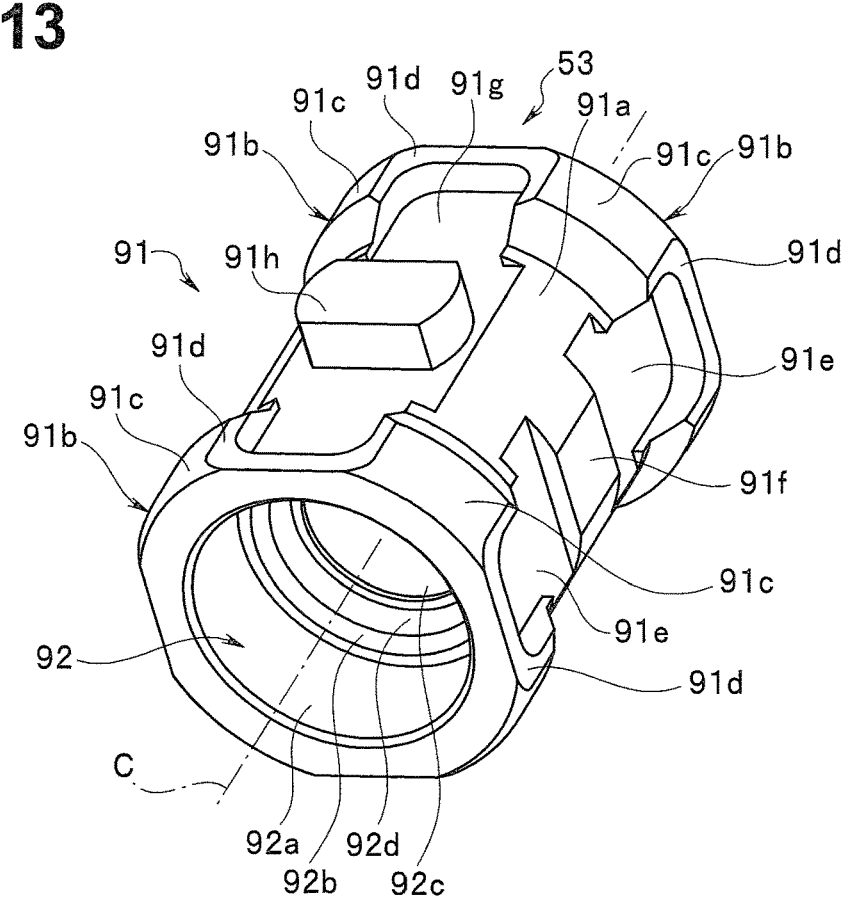
FIG. 13 is a perspective view illustrating a configuration of a movable section 53 according to the embodiment.

FIG. 13 is a perspective view illustrating a configuration of the movable section 53. The movable section 53 illustrated in the drawing includes a tubular-shaped member that has an outer circumferential portion 91 and an inner circumferential portion 92. Hereinafter, the central axis of the movable section 53 will also be referred to as an axis C. This is because the central axis of the movable section 53 coincides with the central axis of the fixed section main body 56 at the time of assembly.

The outer circumferential portion 91 has a tubular section 91a and two projecting edge portions 91b formed at both end portions of the tubular section 91a in the axis C direction and having a larger outer circumferential diameter than the diameter of the tubular section 91a. The tubular section 91a and the projecting edge portions 91b may be configured as an integrated member or may be configured as separate members.

Each projecting edge portion 91b has movable-side sliding surfaces 91c formed of an outer circumferential surface of the projecting edge portion 91b and plane portions 91d that are formed at a part of the projecting edge portion 91b located outward in the radial direction. In the case illustrated in FIG. 13, each projecting edge portion 91b alternately has four movable-side sliding surfaces 91c and four plane portions 91d in the circumferential direction around the axis C at equal intervals. Each of the plane portions 91d lies in the same plane as respective one of four plane portions 91d formed on the side of the other end along the axis C. In other words, the outer circumferential portion 91 have four sets of two plane portions 91d that are formed at mutually different end portions and lie in the same plane.

In each of three sets out of the four sets, a step portion 91e that is formed inward in the radial direction as compared with the tubular section 91a and has a plane-shaped outer circumferential surface is provided between the two plane portions 91d. A notch portion 91f with a plane-shaped outer circumference is provided by chipping the surface of the tubular section 91a at the center of the step portion 91e, which is formed between the two plane portions 91d in each set, in the axis C direction.

A step portion 91g with a plane-shaped outer circumferential surface is also provided between the two plane portions 91d of the remaining one set out of the four sets by being formed inward in the radial direction as compared with the tubular section 91a. A rotation restricting section 91h configured to restrict rotation of the movable section 53 about the axis C is provided at the center of the step portion 91g in the axis C direction so as to project from the outer circumferential surface of the step portion 91g.

A part of a side surface of the rotation restricting section 91h that comes into contact with the fixed section 52 has a bent R shape while side surfaces that respectively face the first magnet 36a and the second magnet 36b have plane shapes. In other words, the surface of the projecting surface of the rotation restricting section 91h that is parallel to the axis C has a shape obtained by respectively chipping a circle with straight lines in a direction that perpendicularly intersects with the axis C on the side of the object and on the side of the image of the axis C and has a shape surrounded by two arcs and two straight lines. Note that the surface of the rotation restricting section 91h that is parallel to the axis C may have a circular shape with a diameter of the length of the rotation restricting section 91h in the axis C direction illustrated in FIG. 13. Alternatively, the surface of the rotation restricting section 91h that is parallel to the axis C may have a rectangular shape.

As illustrated in FIG. 4, the width of the plane of the rotation restricting section 91h that is perpendicularly intersects with the axis C in the circumferential direction is greater than the width of each of the magnets 36a and 36b (the second magnet 36b is illustrated in FIG. 4) in the circumferential direction in the same plane.

The inner circumferential portion 92 has a first inner circumferential portion 92a, a second inner circumferential portion 92b, a third inner circumferential portion 92c, and an inner circumference-side projecting portion 92d. The diameter of the second inner circumferential portion 92b is smaller than diameters of the first inner circumferential portion 92a and the third inner circumferential portion 92c. The inner circumference-side projecting portion 92d with the smallest diameter projecting inward in the radial direction is provided between the second inner circumferential portion 92b and the third inner circumferential portion 92c.

The movable section 53 holds the movable lens group Gv. Specifically, the second inner circumferential portion 92b of the movable section 53 holds a first movable lens Lv1 that the movable lens group Gv has. As illustrated in FIGS. 5 and 6, the first movable lens Lv1 on the side of the image preferably abuts on the inner circumference-side projecting portion 92d.

The movable section 53 is inserted into the fixed section main body 56 with the movable-side sliding surfaces 91c being brought into contact with the fixed-side sliding surface 63. As illustrated in FIGS. 5 and 6, the movable section 53 is inserted such that the inside of the third inner circumferential portion 92c in the radial direction faces the first outer circumferential portion 81a of the rear frame section 55. In this manner, at least a part of the image-side fixed lens group Gb is present inside the third inner circumferential portion 92c of the movable section 53 in the radial direction. In the embodiment, in a case in which the movable section 53 has moved closest to the side of the object, at least a part of the object-side fixed lens group Gf is present inside the first inner circumferential portion 92a of the movable section 53 in the radial direction.

As described above, the movable section 53 has a tubular shape, is disposed inside the fixed section main body 56, is movable along the central axis C of the tubular-shaped fixed section main body 56, and holds one lens or two or more lenses. The magnet section 36 is provided at the movable section 53.

The movable section 53 with the aforementioned configuration is configured using a material such as stainless steel, aluminum, or a resin, for example.

(Configuration of Voice Coil Motor 32)

Next, a configuration of the voice coil motor 32 will be described. The voice coil motor 32 has the coil section 101 disposed at the fixed section main body 56 of the fixed section 52 and the magnet section 36 disposed at the movable section 53 so as to face the inner circumferential portion of the coil section 101, as illustrated in FIG. 3.

The coil section 101 is formed by winding coil wires around the outer circumferential portion of the fixed section main body 56.

Specifically, the coil section 101 has the first coil 101a formed by winding coil wires around an outer circumference of the tubular section 61 of the fixed section main body 56 and the second coil 101b disposed so as to be aligned with the first coil 101a along the axis C and formed by winding coil wires around the outer circumference of the tubular section 61 of the fixed section main body 56 as illustrated in FIGS. 5 and 6. Note that the coil section 101 wound in advance may be disposed later. The first coil 101a and the second coil 101b that are adjacent to each other along the axis C are preferably connected in series but may be connected in parallel.

The first coil 101a and the second coil 101b have plane portions 101ap and 101bp that face the punched sections 61a in the fixed section main body 56, respectively, as illustrated in FIG. 5. The first coil 101a and the second coil 101b also have cylindrical portions 101at and 101bt that face the tubular section 61, respectively, as illustrated in FIG. 6. At the first coil 101a, the four plane portions 101ap and the four cylindrical portions 101at are alternately disposed in a section that perpendicularly intersects with the axis C. Similarly, the four plane portions 101bp and the four cylindrical portions 101bt are alternately disposed in a section that perpendicularly intersects with the axis C at the second coil 101b as well (see FIG. 4).

The magnet section 36 has four sets each including one first magnet 36a and one second magnet 36b disposed so as to face the plane portions 101ap and 101bp and aligned along the axis C inside the plane portions 101ap of the first coil 101a and the plane portions 101bp of the second coil 101b as illustrated in FIGS. 3 to 6. The first magnet 36a and the second magnet 36b in each set are disposed so as to be aligned along the axis C.

The four first magnets 36a and the four second magnets 36b in the four sets aligned along the axis C are disposed at equal intervals at every 90 degrees in the circumferential direction in the section that perpendicularly intersects with the axis C. The rotation restricting section 91h is located between the first magnet 36a and the second magnet 36b of one set out of the four sets.

It is possible to stably place the first magnets 36a and the second magnets 36b by employing such disposition. As a result, the voice coil motor 32 forms a stable magnetic field, and it is possible to curb deviation of the movable section 53 configured to move with respect to the fixed section 52. Note that although the magnets 36a and 36b are placed at every 90° around the axis C in the embodiment, the magnets 36a and 36b may be placed at other angular intervals.

As illustrated in FIGS. 5 and 6, the total of the widths of the first magnets 36a and the second magnets 36b in the axis C direction is shorter than the total of the widths of the first coil 101a and the second coil 101b in the axis C direction. In this manner, it is possible to allow the first magnets 36a and the second magnets 36b to be present within the widths of the first coil 101a and the second coil 101b in the axis C direction, respectively, within the moving range of the movable section 53.

Figure 14:
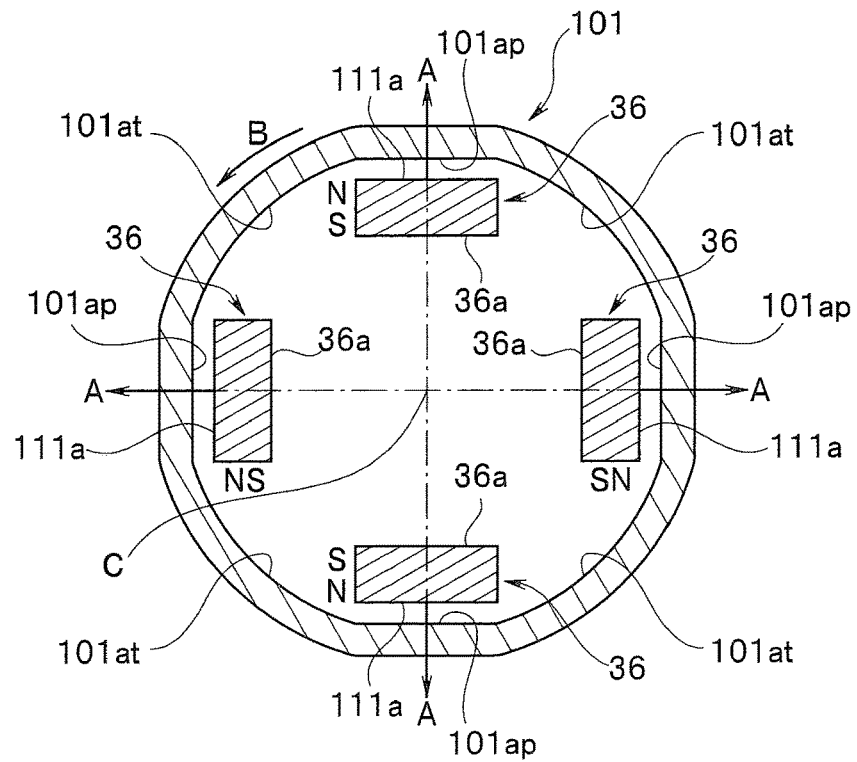
FIG. 14 is a diagram illustrating a configuration of only a voice coil motor when seen in a cut plane passing through the line XIV-XIV illustrate in FIG. 5.
Figure 15:
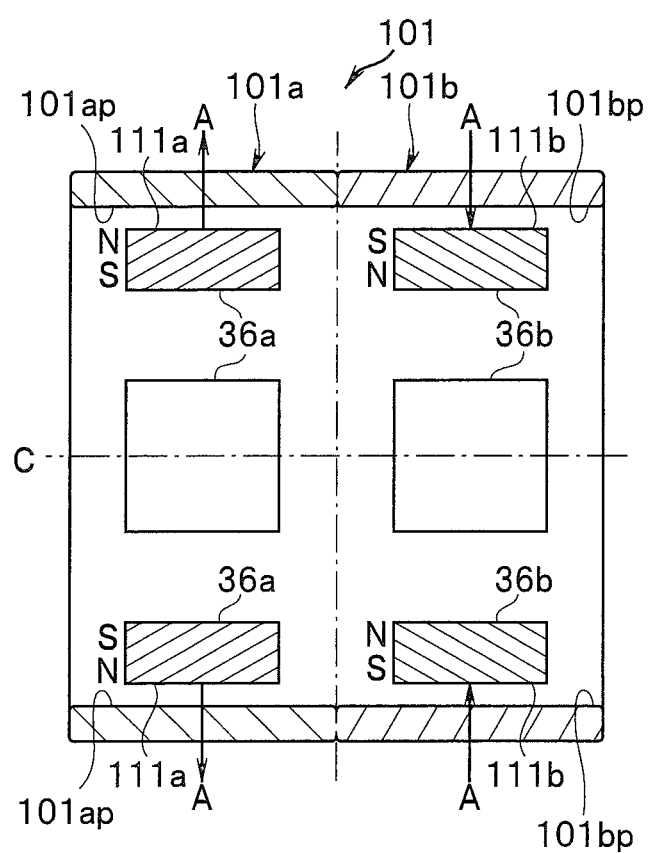
FIG. 15 is a diagram illustrating only the voice coil motor in the same section as the section in FIG. 5 according to the embodiment.

FIG. 14 is a diagram illustrating a configuration of only the voice coil motor when seen in the cut plane passing through the line XIV-XIV illustrated in FIG. 5. FIG. 15 is a diagram illustrating only the voice coil motor in the same section as that in FIG. 5.

As illustrated in FIG. 15, the first magnet 36a and the second magnet 36b in a set are disposed away from each other along the axis C. Further, as illustrated in FIGS. 14 and 15, the magnet section 36 has a plurality of magnets disposed at equal angles around the central axis C, and the respective magnets have undergone magnetic polarization in the direction that perpendicularly intersects with the central axis C. The first magnet 36a and the second magnet 36b in each set are respectively magnetized in the radial direction, and magnetic poles are directed in opposite directions from each other.

In the case illustrated in FIGS. 14 and 15, the four first magnets 36a have N poles on the side of the first coil 101a and S poles on the opposite side, and the four second magnets 36b have S poles on the side of the second coil 101b and N poles on the opposite side. In this case, the magnetic polarization direction of the first magnet 36a and the second magnet 36b in each set perpendicularly intersect with the axis C as represented by the arrow A illustrated in FIGS. 14 and 15. Note that more generally, the magnetic polarization direction of the first magnet 36a and the second magnet 36b in each set may be any direction as long as the direction intersects the axis C.

As illustrated in FIG. 4, the Hall device 37 that is a magnetic sensor is disposed outside the coil section 101 in the radial direction so as to face at least one of the plurality of magnets.

In the embodiment, a winding direction of the coil section 101 is preferably inverted between the set of first magnets 36a and the set of second magnets 36b in the respective sets. In a case in which the first coil 101a is wound in the direction of the arrow B as illustrated in FIG. 14, the second coil 101b may be wound in the opposite direction. Alternatively, the winding directions of the first coil 101a and the second coil 101b may be the same, and the first coil 101a and the second coil 101b may be connected such that current directions are opposite. In this case, it is only necessary for the current to flow in the direction opposite to the arrow B to the second coil 101b when the current directed as the arrow B is caused to flow through the first coil 101a as illustrated in FIG. 14.

As described above, the coil section 101 has the first coil 101a and the second coil 101b aligned along the central axis C. The magnet section 36 includes the plurality of first magnets 36a disposed inside the first coil 101a in the circumferential direction and the plurality of second magnets 36b disposed inside the second coil 101b in the circumferential direction. The magnetic polarization direction of the plurality of first magnets 36a and the magnetic polarization direction of the plurality of second magnets 36b are opposite to each other, and the first coil 101a and the second coil 101b are connected such that directions of the supplied current are inverted.

In the optical unit 51 with the aforementioned configuration, the movable section 53 on which the four magnets 36a are respectively placed so as to face the first coil 101a is disposed inside the fixed section main body 56, around which the first coil 101a is wound, in the radial direction. Therefore, the plane portions 101ap of the first coil 101a are respectively present in the magnetic field in directions that perpendicularly intersects the surfaces 111a outside the first magnets 36a in the radial direction. Note that the four second magnets 36b are also configured in a similar manner.

Therefore, driving efficiency is improved, and it is possible to quickly move the movable section 53. In addition, it is possible to easily assemble the optical unit 51 by forming the surfaces 111a outside the first magnets 36a in the radial direction and the surfaces 111b outside the second magnets 36b in the radial direction into plane shapes.

If a current is caused to flow through the coil section 101 of the optical unit 51, a force in the axis C direction is generated in the movable section 53 due to influences of the magnetic field of the magnet section 36, and the movable section 53 moves in the axis C direction with respect to the fixed section 52. It is possible to cause the movable section 53 to move with respect to the fixed section 52 by controlling currents to be caused to flow through the first coil 101a and the second coil 101b, respectively, for example. Even in a state where the movable section 53 moves with respect to the fixed section 52, the outer surface of the magnet section 36 in the radial direction is disposed in the punched sections 61a of the fixed section main body 56.

The outer circumferential surfaces of the projecting edge portions 91b of the movable section 53 configure the movable-side sliding surfaces 91c that come into contact with the fixed-side sliding surface 63 of the fixed section main body 56 in the optical unit 51 as illustrated in FIG. 6. It is possible to cause the movable section 53 to move with respect to the fixed section main body 56 in a state in which the movable section 53 is constantly in contact with the fixed section main body 56, to curb inclination of the movable section 53 with respect to the fixed section 52, and to cause the movable section 53 to appropriately move by bringing the fixed-side sliding surface 63 of the fixed section main body 56 and the movable-side sliding surfaces 91c of the movable section 53 into contact with each other.

(Position Control of Movable Section)

Next, a method for controlling the position of the movable section will be described.

Figure 16:
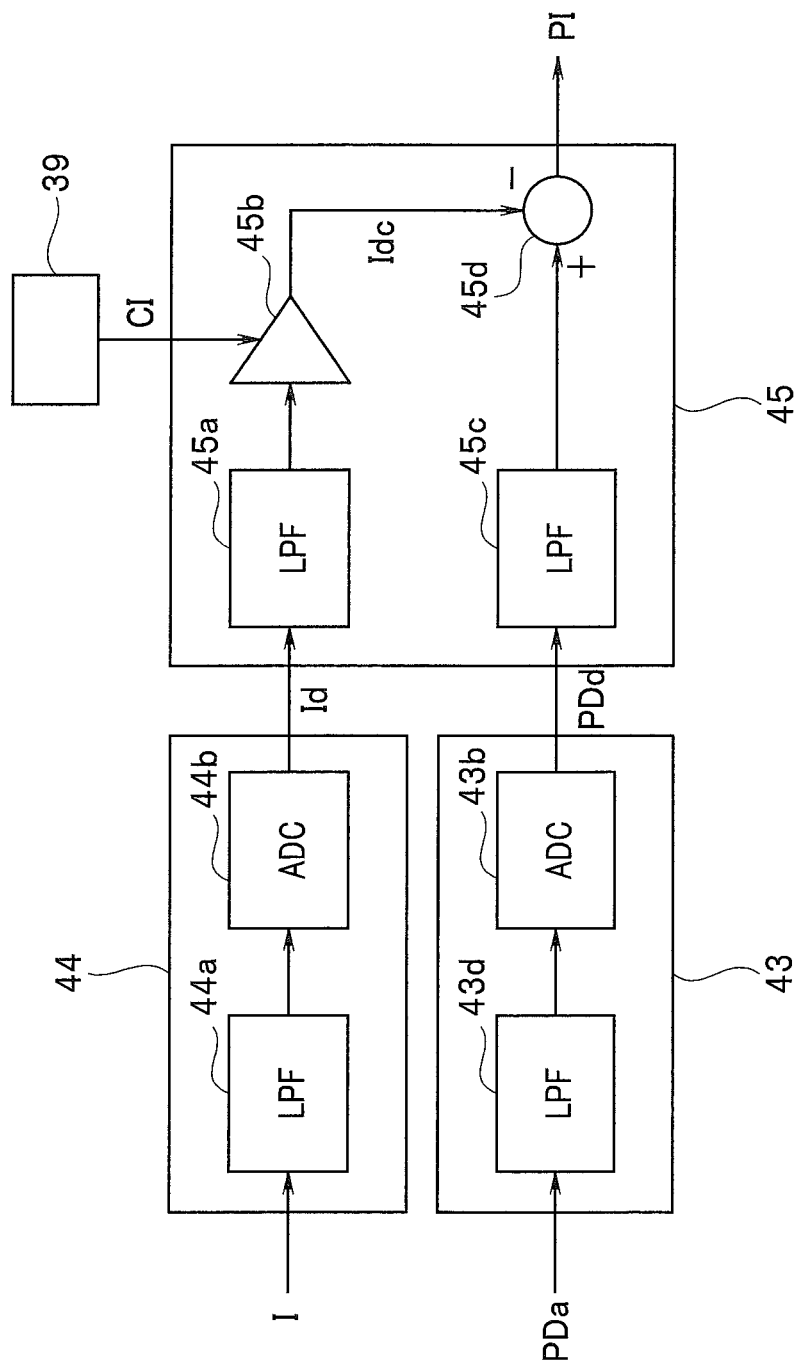
FIG. 16 is a block diagram illustrating configurations of a position detection section 43, a current detection section 44, and an arithmetic operation section 45 in a video processor 3 according to the embodiment.

FIG. 16 is a block diagram illustrating configurations of the position detection section 43, the current detection section 44, and the arithmetic operation section 45 in the video processor 3.

The position detection section 43 detects the position of the magnet section 36 based on the outputted signal of the sensor section 33. The position detection section 43 is a circuit that includes an analog-to-digital conversion circuit (hereinafter, referred to as an ADC) 43b and an analog low pass filter (LPF) 43d that has a predetermined cutoff frequency.

The analog low pass filter 43d receives the sensor output signal PDa from the sensor section 33 and outputs a signal at a predetermined low frequency to the ADC 43b. The ADC 43b converts the voltage of the inputted signal into a digital signal and outputs the digital signal as the sensor output signal PDd to the arithmetic operation section 45.

The current detection section 44 detects the magnitude of the current flowing through the coil section 101. Therefore, the current detection section 44 is a circuit including an analog low pass filter (LPF) 44a that has a predetermined cutoff frequency and an ADC 44b.

The analog low pass filter 44a receives the current signal I from the voice coil motor 32 and outputs a signal at a predetermined low frequency to the ADC 44b. The ADC 44b converts the voltage of the inputted signal into a digital signal and outputs the digital signal as a digital current signal Id in accordance with the analog current signal I to the arithmetic operation section 45.

The arithmetic operation section 45 is a processor configured to correct the sensor output signal PDd that is a position signal indicating the position of the magnet section 36 detected by the position detection section 43 using the correction information CI stored in the memory 39 and output the sensor output signal PDd. More specifically, the arithmetic operation section 45 corrects the sensor output signal PDd that is a position signal indicating the position of the magnet section 36 with the current value of the digital current signal Id detected by the current detection section 44 and the correction information CI.

The arithmetic operation section 45 is a circuit including a digital low pass filter 45a, an amplification circuit 45b, a digital low pass filter 45c, and an addition circuit 45d. Both the digital low pass filters 45a and 45c have predetermined cutoff frequencies.

The digital low pass filter 45a receives the digital current signal Id and outputs the digital current signal Id at a predetermined low frequency to the amplification circuit 45b.

The amplification circuit 45b holds the correction information CI read from the memory 39 and outputs a correction signal Idc, which is a current signal obtained by correcting the digital current signal Id from the digital low pass filter 45a with the correction information CI, to the addition circuit 45d.

The correction information CI is information related to the amount of noise components due to a leaking magnetic flux from the voice coil motor 32.

Noise components included in the outputted signal of the Hall device 37 are proportional to the magnitude of the drive current DI supplied to the coil section 101. Therefore, the correction information CI here is a proportionality coefficient α.

The amplification circuit 45b outputs a correction signal Idc that is proportional to the noise components due to the leaking magnetic flux from the coil section 101 by multiplying the current value of the digital current signal Id by the proportionality coefficient α.

Note that although the correction information CI here is the proportionality coefficient α, the correction information CI may be table data configured to store the correction signal Idc corresponding to the noise components in accordance with the value of the inputted digital current signal Id. In the case, the amplification circuit 45b reads and holds the table data from the memory 39, outputs a correction amount corresponding to the current value of the inputted digital current signal Id based on the table data, and outputs the correction signal Idc corresponding to the value of the inputted digital current signal Id.

The digital low pass filter 45c receives the sensor output signal PDd and outputs a signal at a predetermined low frequency to the addition circuit 45d.

The sensor output signal PDd and the correction signal Idc are inputted to the addition circuit 45d, and the addition circuit 45d outputs a signal of a difference of the correction signal Idc indicating the noise components from the sensor output signal PDd as lens position information PI to the drive control section 42.

In other words, the arithmetic operation section 45 calculates a correction amount by multiplying the current value of the digital current signal Id by the proportionality coefficient α, corrects the sensor output signal PDd by adding or subtracting the correction amount to or from the sensor output signal PDd that is a position signal, and outputs the sensor output signal PDd as lens position information PI to the drive control section 42.

Note that the arithmetic operation section 45 may be configured of a processor including a central processing unit (CPU), a ROM, and a RAM and may perform all or a part of the aforementioned arithmetic operations by a program stored in the ROM.

The drive control section 42 controls a current or a voltage at the coil section 101 based on the lens position information PI that is an arithmetic operation result of the arithmetic operation section 45.

Note that it is necessary to cause the amount of delay and the amount of attenuation of the current signal I at the timing of subtraction of the addition circuit 45d to coincide with the amount of delay and the amount of attenuation of the sensor output signal PD from the sensor section 33 in order to accurately correct the position of the lens 35a. Therefore, the cutoff frequency of the analog low pass filter 44a and the cutoff frequency of the digital low pass filter 45c coincide with each other, and the cutoff frequency of the analog low pass filter 43d and the cutoff frequency of the digital low pass filter 45a coincide with each other.

As described above, the arithmetic operation section 45 outputs the lens position information PI, from which the noise components due to the leaking magnetic flux of the coil section 101 of the voice coil motor 32 have been removed, to the drive control section 42. Therefore, since the drive control section 42 outputs, to the voice coil motor driver 41, the driving command signal DS for causing the lens 35a to move to the focusing position designated through a command using the focusing position command signal FC from the focal point control section 46, it is possible to precisely control the position of the movable section 53.

Therefore, according to the aforementioned embodiment, it is possible to provide an endoscope apparatus capable of removing influences of a leaking magnetic field from the coil and highly precisely controlling the position of the movable section when the movable section is driven to move forward and backward using the voice coil motor.

Note that although the example of the control of the position of the lens 35a for focusing control has been described as the movable section in the aforementioned embodiment, the aforementioned embodiment can also be applied to control of a position of a lens for zooming control as the movable section.

As illustrated in FIG. 1, for example, a zooming operation device 25 configured to drive a zooming lens, which will be described later, is provided along with various operation devices such as a release button at the operation section 12. A button 25a configured to perform zooming on a telephoto side and a button 25b configured to perform zooming on a wide side of a zooming mechanism are provided in the zooming operation device 25. If the user presses the button 25a, the zooming operation device 25 outputs a signal to cause the zooming lens to move to perform zooming on the telephoto side while the button 25a is being pressed, and the zooming lens is then stopped at a zooming position at the point when the pressing of the button 25a is released.

Similarly, if the user presses the button 25b, the zooming operation device 25 outputs a signal to cause the zooming lens to move to perform zooming on the wide side while the button 25b is being pressed, and the zooming lens is then stopped at a zooming position at the point when the pressing of the button 25b is released. Therefore, the user can observe the object at a desired zooming position or with a desired amount of zooming through the pressing operations on the buttons 25a and 25b.

Note that although the zooming operation device 25 is shown as the two buttons 25a and 25b provided at the operation section 12 of the endoscope 2 here, the zooming operation device 25 may be another operation device such as a foot switch connected to the video processor 3.

The user can cause the monitor 4 to display an endoscope image at an image angle that the user desires through an operation on the zooming operation device 25. The video processor 3 drives an actuator of the endoscope 2 in response to the operation performed by the user on the zooming operation device 25.

The zooming lens is fixed to the movable section 53 of the voice coil motor 32, and the sensor section 33 outputs the sensor output signal PDa indicating the position of the magnet section 36.

If the user presses the aforementioned button 25a or 25b, a zooming command signal ZC is outputted from the zooming operation device 25 as represented by the two-dotted dashed line in FIG. 2. The drive control section 42 outputs the driving command signal DS for driving the voice coil motor 32 based on the zooming command signal ZC from the zooming operation device 25 and the lens position information PI from the arithmetic operation section 45 and causes the zooming lens to move. The zooming position of the image pickup optical system 35 changes with the movement of the zooming lens, and as a result, the size of the object image displayed on the monitor 4 changes.

Therefore, the aforementioned embodiment can also be applied to control of the position of the lens for zooming control using the voice coil motor based on the focal point position signal.

Further, although the correction information CI is stored in the memory 39 provided in the endoscope 2 and the video processor 3 corrects the position signal using the correction information CI read from the memory 39 of the endoscope 2 in the aforementioned embodiment, the video processor 3 may have a memory (not illustrated) that stores the correction information CI.

For example, information such as a manufacturing number of the endoscope 2 is stored as individual information in the memory 39 of the endoscope 2, and correction information CI associated with the information such as the manufacturing number is stored in the memory of the video processor 3. Therefore, even if the endoscope 2 does not have the correction information, the arithmetic operation section 45 can correct the position signal using the correction information read from the memory of the video processor 3 based on the information such as the manufacturing number.

According to the aforementioned embodiment, it is possible to provide an endoscope apparatus capable of removing influences of a leaking magnetic field from the coil and highly precisely controlling the position of the movable section when the movable section is driven to move forward and backward using the voice coil motor as described above.

The invention is not limited to the aforementioned embodiment, and various modifications, changes, and the like can be made without changing the gist of the invention.

What is claimed is:

1. An endoscope apparatus comprising
an endoscope;
a fixed section main body having a tubular shape;
a tubular-shaped movable member disposed inside the fixed section main body and configured to be movable along a central axis of the tubular shape and hold a lens;
a voice coil motor provided in the endoscope and including a magnet and a coil such that the magnet is movable with respect to the coil, wherein the coil is formed by winding a coil wire around an outer circumferential portion of the fixed section main body and the magnet is provided at the movable member;
a tubular-shaped sensor fixed member into which the fixed section main body is inserted along the central axis, wherein the sensor fixed member has a hole configured to position the magnetic sensor, the coil is disposed inside the sensor fixed member, and the sensor fixed member has a hole through which the coil wire of the coil is caused to pass;
a magnetic sensor disposed in a vicinity of the coil and configured to detect a magnetic field of the magnet in order to detect a position of the magnet;
a memory configured to store correction information;
a position detection circuit configured to detect the position of the magnet from an outputted signal of the magnetic sensor;
a processor configured to correct a position signal indicating the position of the magnet detected by the position detection circuit using the correction information stored in the memory and output the position signal; and
a drive control circuit configured to control a current or a voltage to the coil based on an arithmetic operation result of the processor.

2. The endoscope apparatus according to claim 1, further comprising:
a current detection circuit configured to detect a magnitude of the current flowing through the coil,
wherein the processor corrects the position signal with a current value of the current detected by the current detection circuit and the correction information.

3. The endoscope apparatus according to claim 2,
wherein the correction information is a proportionality coefficient, and
the processor calculates a correction amount by multiplying the current value by the proportionality coefficient and corrects the position signal by adding or subtracting the correction amount to or from the position signal.

4. The endoscope apparatus according to claim 2,
wherein the correction information is table data configured to store a correction amount corresponding to the current value, and
the processor reads and holds the table data from the memory, outputs the correction amount corresponding to the current value based on the table data, and adds or subtracts the correction amount to or from the position signal to correct the position signal.

5. The endoscope apparatus according to claim 1, further comprising:
an urging member that is a magnetic body provided at the sensor fixed member,
wherein the urging member is disposed to attract the magnet in an outer diameter direction of the sensor fixed member.

6. The endoscope apparatus according to claim 1,
wherein the magnet is disposed in plurality at an equal angle around the central axis, and each magnet undergoes magnetic polarization in a direction that perpendicularly intersects with the center axis.

7. The endoscope apparatus according to claim 6,
wherein the magnetic sensor is disposed outward in a radial direction of the coil to face at least one of the plurality of magnets.

8. The endoscope apparatus according to claim 1,
wherein the coil has a first coil and a second coil aligned along the central axis,
the magnet comprises a plurality of first magnets disposed along a circumference inside the first coil and a plurality of second magnets disposed along a circumference inside the second coil,
a direction of magnetic polarization of the plurality of first magnets and a direction of magnetic polarization of the plurality of second magnets are opposite to each other, and
the first coil and the second coil are connected such that directions of currents supplied are inverted.

9. The endoscope apparatus according to claim 1,
wherein the magnetic sensor is located between an end surface of the magnet on a side in a first moving direction when the magnet moves in the first direction along the central axis and an end surface of the magnet on a side in a second moving direction that is a direction opposite to the first direction when the magnet moves in the second direction along the central axis.

10. The endoscope apparatus according to claim 1,
wherein the lens is a lens for focusing control or for zooming control in an objective optical system.

11. The endoscope apparatus according to claim 1,
wherein the magnetic sensor is disposed outward in a radial direction of the coil to face the magnet, and
the endoscope apparatus has an urging member that is a magnetic body disposed outside the magnetic sensor in the radial direction of the coil to face the magnetic sensor and configured to attract the magnet in the radial direction of the coil and increase a magnetic force of the magnet using a yoke function at a position of the magnetic sensor.

12. The endoscope apparatus according to claim 11,
wherein, in defining a position of an end surface of the magnet on a side of an object when the movable member moves closest to the side of the object as P1 and a position of an end surface of the magnet on a side of an image when the movable member moves closest to the side of the image as P2, a length of the urging member in a direction of the central axis is equal to or greater than a range between the position P1 and the position P2, and the urging member is disposed to include the range between the position P1 and the position P2 in the direction of the central axis.

* * * * *